United States Patent [19]

Duggan et al.

[11] Patent Number: 5,130,306
[45] Date of Patent: Jul. 14, 1992

[54] 5-OXYGENATED HMG-COA REDUCTASE INHIBITORS

[75] Inventors: Mark E. Duggan, Wynnewood; George D. Hartman, Lansdale, both of Pa.

[73] Assignee: Merck & Co., Inc., Rahway, N.J.

[21] Appl. No.: 533,746

[22] Filed: Jun. 6, 1990

Related U.S. Application Data

[62] Division of Ser. No. 322,398, Mar. 13, 1989, Pat. No. 4,963,538.

[51] Int. Cl.$^5$ ............ A61K 31/66; A61K 31/22; C07C 69/013; C07C 271/38
[52] U.S. Cl. .................. 514/121; 514/480; 514/510; 558/198; 560/27; 560/32; 560/119; 560/255; 560/256
[58] Field of Search .............. 560/256, 119, 32, 27, 560/32, 255; 514/510, 480, 121; 558/198

[56] References Cited

U.S. PATENT DOCUMENTS

| | | | |
|---|---|---|---|
| 4,420,491 | 12/1983 | Albers-Schonberg et al. | 560/256 |
| 4,444,784 | 4/1984 | Hoffman et al. | 560/256 |
| 4,450,171 | 5/1984 | Hoffman et al. | 560/256 |
| 4,668,699 | 5/1987 | Hoffman et al. | 560/256 |
| 4,851,436 | 7/1989 | Hoffman et al. | 560/256 |
| 4,866,093 | 9/1989 | Terahara et al. | 560/256 |

FOREIGN PATENT DOCUMENTS 186972 10/1984 Japan.

OTHER PUBLICATIONS

Alberts, A. W., *American Journal of Cardiology*, 62, pp. 105–155 (1988).
Stokker, G. E. et al., *J. Med. Chem.* 28, pp. 347–358 (1985).

*Primary Examiner*—Mary C. Lee
*Assistant Examiner*—Michael G. Ambrose
*Attorney, Agent, or Firm*—Melvin Winokur; Joseph F. DiPrima

[57] ABSTRACT

Novel HMG-CoA reductase inhibitors are useful as antihypercholesterolemic agents and are represented by structural formulae (I) or (II):

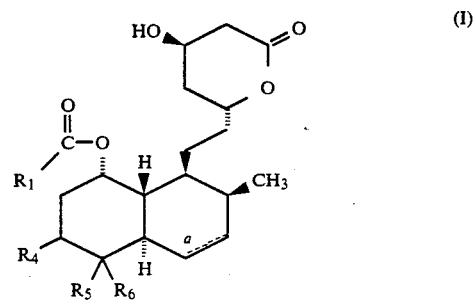

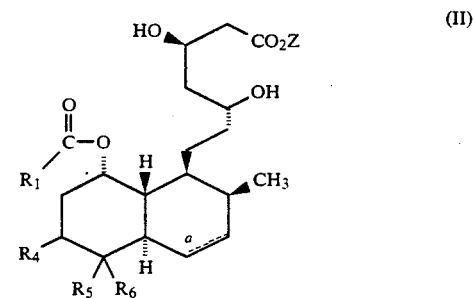

wherein position 5 of the polyhydronaphthyl ring is singly or doubly bonded to oxygen or incorporated into a $C_{3-7}$ carbocyclic ring.

19 Claims, No Drawings

5-OXYGENATED HMG-COA REDUCTASE INHIBITORS

This is a division of application Ser. No. 322,398 filed Mar. 13, 1989 now U.S. Pat. No. 4,963,538.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR ® (lovastatin), now commercially available, is one of a group of very active antihypercholesterolemic agents that function by limiting cholesterol biosynthesis by inhibiting the enzyme, hydroxymethylglutaryl coenzyme A CHMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

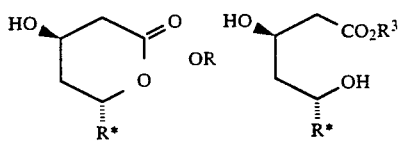

wherein:

$R^3$ is hydrogen, $C_{1-5}$ alkyl or $C_{1-5}$ alkyl substituted with a member of the group consisting of phenyl, dimethylamino, or acetylamino; and $R^*$ is

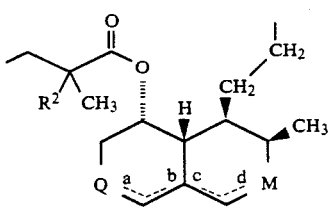

wherein Q is

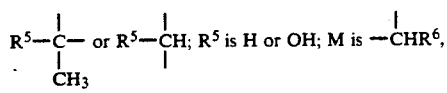

$R^5$ is H or OH; M is $-CHR^6$, $R^6$ is hydrogen or hydroxy;

$R^2$ is hydrogen or methyl; and a, b, c, and d represent single bonds, one of a, b, c or d represents a double bond, or both a and c or both b and d represent double bonds provided that when a is a double bond, Q is

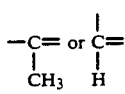

and when d is a double bond, M is

U.S. Pat. No. 4,517,373 discloses semi-synthetic hydroxy containing compounds represented by the above general formula wherein $R^*$ is

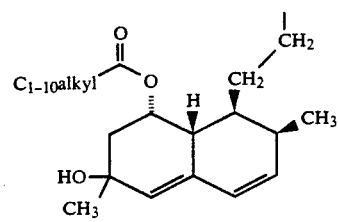

AND

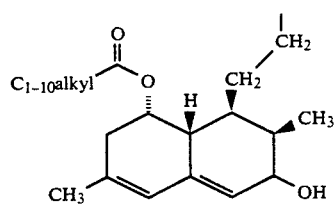

U.S. Pat. No. 4,537,859 and U.S. Pat. No. 4,448,979 also disclose semi-synthetic hydroxy-containing compounds represented by the above general formula wherein $R^*$ is

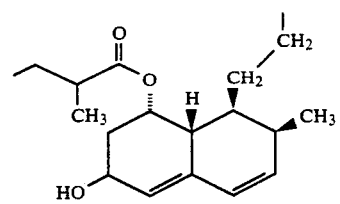

AND

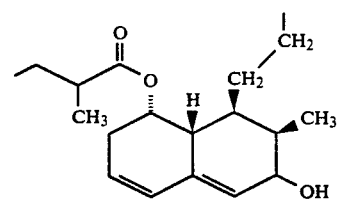

These compounds are prepared by the action of certain microorganisms on the corresponding non-hydroxylated substrates. One such organism described in U.S. Pat. No. 4,537,859 is of the genus Nocardia.

U.K. Pat. No. 2,075,013 discloses semi-synthetic hydroxy containing compounds represented by the above general formula wherein $R^*$ is:

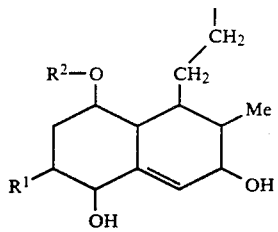

wherein $R^1$ is H or Me, and $R^2$ is H or acyl.

U.S. patent application Ser. No. 048,136 filed May 15, 1987 abandoned, refiled as Ser. No. 533,744, Jun. 6, 1990 discloses 6-substituted compounds of the above general formula wherein R* is:

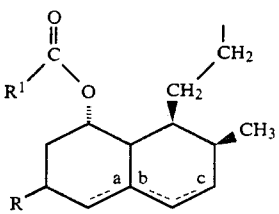

wherein R is $$CH_2OH, \quad CH_2O\overset{O}{\overset{\|}{C}}R^4, \quad CO_2R^7 \text{ or } \overset{O}{\overset{\|}{C}}NR^8R^9;$$

and $R^1$, $R^4$, $R^7$, $R^8$ and $R^9$ are broadly defined organic moieties.

U.S. Pat. Nos. 4,604,472 and 4,733,003 disclose compounds of the above formula wherein R* is:

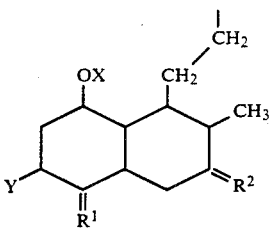

wherein X represents a hydrogen atom or a 2-methylbutyryl group, Y represents a hydrogen atom or a methyl group and $R^1$ and $R^2$ are the same or different and each represents an oxygen atom or a group of formula =N-OR$^3$ where $R^3$ is a hydrogen or alkyl moiety.

DETAILED DESCRIPTION OF THE INVENTION

This invention relates to HMG-CoA reductase inhibitors of formulae (I) and (II):

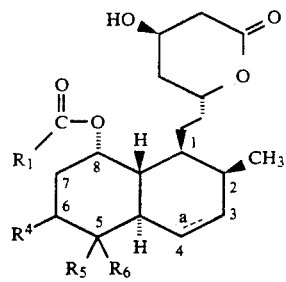

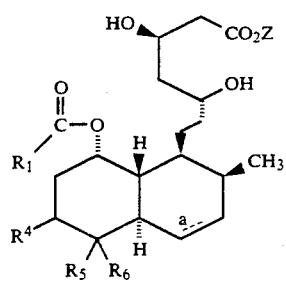

(Numbering relates to positions in tetrahydronaphthyl ring).

wherein:

$R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkylS(O)$_n$ in which n is 0 to 2,
  (j) $C_{3-8}$ cycloalkylS(O)$_n$,
  (k) phenylS(O)$_n$,
  (l) substituted phenylS(O)$_n$ in which the substituents are X and Y, and
  (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
  (a) $C_{1-10}$ alkyl
  (b) substituted $C_{1-10}$ alkyl in which the substitutent is selected from
    (i) halogen,
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituents are X and Y
    (viii) $C_{1-10}$ alkylS(O)$_n$,
    (ix) $C_{3-8}$ cycloalkylS(O)$_n$,
    (x) phenylS(O)$_n$,
    (xi) substituted phenylS(O)$_n$ in which the substituents are X and Y, and (xii) oxo,
(c) $C_{1-10}$ alkyl$S(O)_n$,
(d) $C_{3-8}$ cycloalkyl$S(O)_n$,
(e) phenyl$S(O)_n$,
(f) substituted phenyl$S(O)_n$ in which the substituents are X and Y,
(g) halogen,
(h) hydroxy,
(i) $C_{1-10}$ alkoxy,
(j) $C_{1-5}$ alkoxycarbonyl,
(k) $C_{1-5}$ acyloxy,
(l) phenyl, and
(m) sustituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
  (a) piperidinyl,
  (b) pyrrolidinyl,
  (c) piperazinyl,
  (d) morpholinyl, and
  (e) thiomorpholinyl; and
(17) $R_{10}S$ in which $R_{10}$ is selected from
  (a) $C_{1-10}$ alkyl,
  (b) phenyl, and
  (c) susbtituted phenyl in which the substituents are X and Y;

$R_4$ is;
(1) hydrogen;
(2) $C_{1-10}$ alkyl; and
(3) substituted $C_{1-10}$ alkyl in which one or more substituents is selected from
  (a) halogen,
  (b) hydroxy,
  (c) $C_{1-10}$ alkoxy
  (d) $C_{1-10}$ alkoxycarbonyl,
  (e) $C_{1-5}$ alkylacyloxy,
  (f) phenylacyloxy,
  (g) phenoxycarbonyl,
  (h) $C_{1-5}$ alkylacyloxy,
  (i) phenyl $C_{1-5}$ alkoxy,
  (j) amino,
  (k) $C_{1-5}$ alkylamino,
  (l) di($C_{1-5}$ alkyl)amino,
  (m) phenylamino,
  (n) substituted phenylamino in which the substituents are X and Y;
  (o) phenyl $C_{1-5}$ alkylamino,
  (p) substituted phenyl $C_{1-5}$ alkylamino in which the substituents are X and Y,
  (q) $C_{3-8}$ cycloalkyl,
  (r) phenyl,
  (s) substituted phenyl in which the substituents are X and Y,
  (t) phenyl$S(O)_n$,
  (u) substituted phenyl $S(O)_n$ in which the substituents are X and Y,
  (v) phenyl $C_{1-5}$ alkyl $S(O)_n$,
  (w) $C_{1-5}$ alkyl$S(O)_n$;
  (x) phenylaminoacyloxy,
  (y) $C_{1-5}$alkylaminoacyloxy,
  (z) $C_{1-5}$alkylacylamino,
  (aa) di(phenyl$C_{1-5}$alkyl)phosphonyl
  (bb) di($C_{1-5}$alkyl)phosphinyl
(4) $R_4$ together with the carbon atom to which it is attached represents a $C_{3-8}$ carbocyclic ring;

$R_5$ and $R_6$ independently are H, OH, $OR_7$ or $R_5$ and $R_6$ together with the carbon to which they are attached represent C=O or $R_5$ and $R_6$ together with the carbon to which they are attached represent a carbocyclic ring of 3 to 7 atoms; provided that when $R_5$ is H, $R_6$ is OH or $OR_7$, and when $R_5$ is OH, $R_6$ is H, and when $R_5$ is $OR_7$, $R_6$ is H;

$R_7$ is

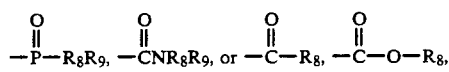

phenyl$C_{1-3}$alkyl, $C_{1-5}$alkyl;

$R_8$ and $R_9$ independently are H, $C_{1-3}$alkyl, phenyl$C_{1-3}$alkyl or aryl wherein aryl is phenyl naphthyl, pyridyl, furanyl, thienyl or phenyl, naphthyl, pyridyl, furanyl or thienyl substituted with groups X and Y provided that when $R_7$ is

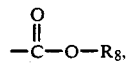

$R_8$ is not H and when $R_7$ is

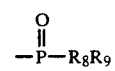

neither $R_8$ nor $R_9$ is H;
X and Y are independently selected from:
  a) OH,
  b) halogen,
  c) trifluoromethyl,
  d) $C_{1-3}$alkoxy,
  e) $C_{1-3}$alkylcarbonyloxy,
  f) phenylcarbonyloxy,
  g) $C_{1-3}$alkoxycarbonyl,
  h) phenyloxycarbonyl,
  i) hydrogen;
  j) $C_{1-5}$alkyl;
Z is selected from
(1) hydrgen;
(2) $C_{1-5}$alkyl;
(3) substituted $C_{1-5}$alkyl in which the substituent is selected from
  (a) phenyl,
  (b) dimethylamino, and
  (c) acetylamino, and
(4) 2,3 hydroxypropyl;
halogen is
  Cl or F;
a is a single bond or a double bond; or a pharmaceutically acceptable salt thereof.

Except where specifically defined to the contrary, the terms "alkyl", "alkenyl", "acyl" "aryloxy" and "alkoxy" include both the straight-chain and branched-chain species of the term.

One embodiment of this invention is the class of compounds of formulae (I) and (II) wherein:

$R_1$ is selected from:
(1) $C_{1-10}$ alkyl;
(2) substituted $C_{1-10}$ alkyl in which one or more substituent(s) is selected from
   (a) halogen,
   (b) hydroxy,
   (c) $C_{1-10}$ alkoxy,
   (d) $C_{1-5}$ alkoxycarbonyl,
   (e) $C_{1-5}$ acyloxy,
   (f) $C_{3-8}$ cycloalkyl,
   (g) phenyl,
   (h) substituted phenyl in which the substituents are X and Y, and
   (i) oxo;
(3) $C_{3-8}$ cycloalkyl;
(4) substituted $C_{3-8}$ cycloalkyl in which one substituent is selected from
   (a) $C_{1-10}$ alkyl,
   (b) substituted $C_{1-10}$ alkyl in which the substituent is selected from
      (i) halogen,
      (ii) hydroxy,
      (iii) $C_{1-10}$ alkoxy
      (iv) $C_{1-5}$ acyloxy,
      (v) $C_{1-5}$ alkoxycarbonyl,
      (vi) phenyl,
      (vii) substituted phenyl in which the substituents are X and Y, and
      (viii) oxo,
   (c) halogen,
   (d) hydroxy,
   (e) $C_{1-10}$ alkoxy,
   (f) $C_{1-5}$ alkoxycarbonyl,
   (g) $C_{1-5}$ acyloxy,
   (h) phenyl,
   (i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y;

$R_4$ is:
(1) hydrogen;
(2) $C_{1-10}$ alkyl;
(3) substituted $C_{1-10}$ alkyl in which one or more substituents is selected from:
   (a) halogen,
   (b) hydroxy,
   (c) amino;
(4) $CH_2R_{12}$ in which $R_{12}$ is selected from:
   (a) $C_{1-5}$ alkoxy,
   (b) $C_{1-5}$ alkoxy carbonyl,
   (c) $C_{1-5}$ alkylacyloxy,
   (d) phenylacyloxy,
   (e) phenoxycarbonyl,
   (f) phenyl$C_{1-5}$alkyl,
   (g) phenyl$C_{1-5}$alkoxy,
   (h) $C_{1-5}$alkylamino,
   (i) di($C_{1-5}$alkyl)amino,
   (j) phenylamino,
   (k) substituted phenylamino in which the substituents are X and Y,
   (l) phenyl $C_{1-5}$alkylamino,
   (m) substituted phenyl $C_{1-5}$ alkyl amino in which the substituents are X and Y,
   (n) $C_{3-8}$ cycloalkyl,
   (o) phenyl,
   (p) substituted phenyl in which the substituents are X and Y,
   (q) phenylS(O)$_n$
   (r) substituted phenylS(O)$_n$ in which the substituents are X and Y,
   (s) phenyl $C_{1-5}$ alkylS(O)$_n$,
   (t) $C_{1-5}$ alkylS(O)$_n$,
   (u) phenylaminoacyloxy,
   (v) $C_{1-5}$ alkylaminoacyloxy,
   (w) $C_{1-5}$ alkylacylamino,
   (x) di(phenyl$C_{1-5}$alkyl)phosphonyl,
   (y) di($C_{1-5}$alkyl)phosphinyl;
(5) $R_4$ together with the carbon atom to which it is attached represents a cyclopropane ring;

$R_5$ and $R_6$ independently are H, OH, OR$_7$ or $R_5$ and $R_6$ together with the carbon to which they are attached represent C=O or $R_5$ and $R_6$ together with the carbon to which they are attached represent a cyclopropane ring; provided that when $R_5$ is H, $R_6$ is OH or OR$_7$, and when $R_5$ is OH, $R_6$ is H, and when $R_5$ is OR$_7$, $R_6$ is H;

$R_7$ is

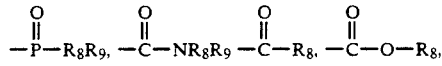

-phenyl$C_{1-3}$alkyl, $C_{1-5}$alkyl;

$R_8$ and $R_9$ independently are H, $C_{1-3}$alkyl, phenyl$C_{1-3}$alkyl or aryl wherein aryl is phenyl naphthyl, pyridyl, furanyl, thienyl or phenyl, naphthyl, pyridyl, furanyl or thienyl substituted with a groups X and Y provided that when $R_7$; is

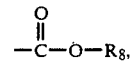

$R_8$ is not H and when $R_7$ is

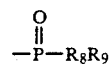

neither $R_8$ nor $R_9$ is H;

X and Y are independently selected from:
a) OH,
b) F,
c) trifluoromethyl,
d) $C_{1-3}$alkoxy,
e) hydrogen;
f) $C_{1-5}$alkyl.

In one subclass are the compounds of formulae (I) and (II) wherein:
$R_1$ is $C_{1-10}$alkyl; and
$R_4$ is $CH_3$, H, or $CH_2$phenyl.

Illustrative of this subclass are those compounds of formulae (I) and (II) wherein;
$R_7$ is

$C_{1-5}$alkyl or phenyl$C_{1-3}$alkyl;

$R_8$ and $R_9$ independently are H, $C_{1-3}$alkyl, phenyl $C_{1-3}$alkyl or aryl wherein aryl is phenyl or naphthyl or phenyl or naphthyl substituted with X;

Further illustrating this subclass are those compounds wherein:

$R_1$ is 2-butyl or 2-methyl-2-butyl;

$R_4$ is $CH_3$.

Exemplifying this subclass are the following compounds:

6(R)-[2-[8(S)-(2,2-dimethylbutyryloxy)-2(S)-methyl-5-(R)-hydroxy-6(R)-methyl-1,2,3,4,4a(R),5,6,7,8,8a(R-)decahydronaphthyl-1(S)]ethyl]-4(R)-hydroxy-3,4,5,6-tetrahydro-2H-pyran-2-one;

6(R)-[2-[8(S)-(2,2-dimethylbutyryloxy)-2(S)-methyl-5-(R)-benzylaminocarbonyloxy-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one;

6(R)-[2-[8(S)-(2,2-dimethylbutyryloxy)-2(S)-methyl-5-(R)-diphenylphosphinyloxy-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one;

6(R)-[2-[8(S)-(2,2-dimethylbutyryloxy)-2(S)-methyl-5-(R)-(1-phenylethyl-2-oxy)-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one;

6(R)-[2-[8(S)-(2,2-dimethylbutyryloxy)-2(S)-methyl-5-(R)-dibenzylaminocarbonyloxy-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2one;

6(R)-[2-[8(S)-(2,2-dimethylbutyryloxy)-2(S)-methyl-5-(R)-hydroxy-6(S)-methyl-1,2,3,4,4a(R),5,6,7,8,8a(R)-decahydronaphthyl-1(S)]ethyl]-4(R)-hydroxy-3,4,5,6-tetrahydro-2H-pyran-2one;

6(R)-[2-[8(S)-(2,2-dimethylbutyryloxy)-2(S)-methyl-5-(S)-hydroxy-6(S)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one;

6(R)-{2-{8(S)-(2,2-dimethylbutyryloxy)-2(S)-methyl-5-oxo-6(R)-methyl-1,2,3,4,4a(R),6,7,8,8a(R)-nonahydronaphthyl-1(S)}ethyl}-4(R)-hydroxy-3,4,5,6-tetrahydro-2H-pyran-2-one;

6(R)-{2-{8(S)-(2,2-dimethylbutyryloxy)-2(S)-methyl-5-oxo-6(S)-methyl-1,2,3,4,4a(R),6,7,8,8a(R)-nonahydronaphthyl-1(S)}ethyl}-4(R)-hydroxy-3,4,5,6-tetrahydro-2H-pyran-2-one;

6(R)-[2-[8(S)-(2,2-dimethylbutyryloxy)-2(S)-methyl-5-(R)-hydroxy-6(R)-methyl-1,2,4a(R),5,6,7,8,8a(R)-octahydronaphthyl-1(S)]ethyl]-4(R)-hydroxy-3,4,5,6-tetrahydro-2H-pyran-2-one; and the corresponding ring opened dihydroxy acids and esters thereof.

In a second subclass are the compounds of formula (I) and formula (II) wherein:

$R_1$ is $C_{1-10}$alkyl; and $R_4$ is $CH_2OH$, or phenylacyloxymethyl.

Illustrative of this subclass are those compounds of formulae (I) and (II) wherein:

$R_7$ is

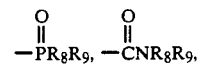

$C_{1-5}$alkyl or phenyl$C_{1-3}$alkyl;

$R_8$ and $R_9$ independently are H, $C_{1-3}$alkyl, phenyl$C_{1-3}$alkyl, or aryl wherein aryl is phenyl or naphthyl or phenyl or naphthyl substituted with X;

Further illustrating this subclass are those compounds wherein:

$R_1$ is 2-butyl or 2-methyl-2-butyl;

$R_4$ is $CH_2OH$.

Exemplifying this subclass are the following compounds:

6(R)-[2-[8(S)-(2,2-dimethylbutyryloxy)-2(S)-methyl-5-(R)-hydroxy-6(R)-hydroxymethyl-1,2,3,4,4a(R),5,6,7,8,8a(R)-decahydronaphthyl-1(S)]ethyl]-4-(R)-hydroxy-3,4,5,6-tetrahydro-2H-pyran-2-one;

6(R)-[2-[8(S)-(2,2-dimethylbutyryloxy)-2(S)-methyl-5-(R)-benzylaminocarbonyloxy-6(R)-hydroxymethyl-1,2,3,4,4a(R),5,6,7,8,8a(R)-decahydronaphthyl-1(S)]ethyl]-4(R)-hydroxy-3,4,5,6-tetrahydro-2H-pyran-2-one;

6(R)-[2-[8(S)-(2,2-dimethylbutyryloxy)-2(S)-methyl-5-(R)-diphenylphosphinyloxy-6(R)-hydroxymethyl-1,2,3,4,4a(R),5,6,7,8,8a(R)-decahydronaphthyl-1(S)]ethyl]-4(R)-hydroxy-3,4,5,6-tetrahydro-2H-pyran-2-one;

6(R)-[2-[8(S)-(2,2-dimethylbutyryloxy)-2(S)-methyl-5-(R)-(1-phenylethyl-2-oxy)-6(R)-hydroxymethyl-1,2,3,4,4a(R),5,6,7,8,8a(R)-decahydronaphthyl-1(S)]ethyl]-4(R)-hydroxy-3,4,5,6-tetrahydro-2H-pyran-2-one;

6(R)-[2-[8(S)-(2,2-dimethylbutyryloxy)-2(S)-methyl-5(R)-dibenzylaminocarbonyloxy-6(R)-hydroxymethyl-1,2,3,4,4$a$(R),5,6,7,8,8$a$(R)-decahydronaphthyl-1(S)]ethyl]-4(R)-hydroxy-3,4,5,6-tetrahydro-2H-pyran-2-one;

6(R)-[2-[8(S)-(2,2-dimethylbutyryloxy)-2(S)-methyl-5(R)-hydroxy-6(S)-hydroxymethyl-1,2,3,4,4$a$(R),5,6,7,8,8$a$(R)-decahydronaphthyl-1(S)]ethyl]-4(R)hydroxy-3,4,5,6-tetrahydro-2H-pyran-2-one;

6(R)-[2-[8(S)-(2,2-dimethylbutyryloxy)-2(S)-methyl-5(S)-hydroxy-6(S)-hydroxymethyl-1,2,3,4,4$a$(R),5,6,7,8,8$a$(R)-decahydronaphthyl-1(S)]ethyl]-4(R)hydroxy-3,4,5,6-tetrahydro-2H-pyran-2-one; and the corresponding ring opened dihydroxy acids and esters thereof.

The compounds of formula (I) are prepared from lovastatin or mevastatin or a 6-desmethyl-6-hydroxymethyl or 8-acyloxy analog thereof, following the outline in Schemes 1 and 2.

SCHEME 1

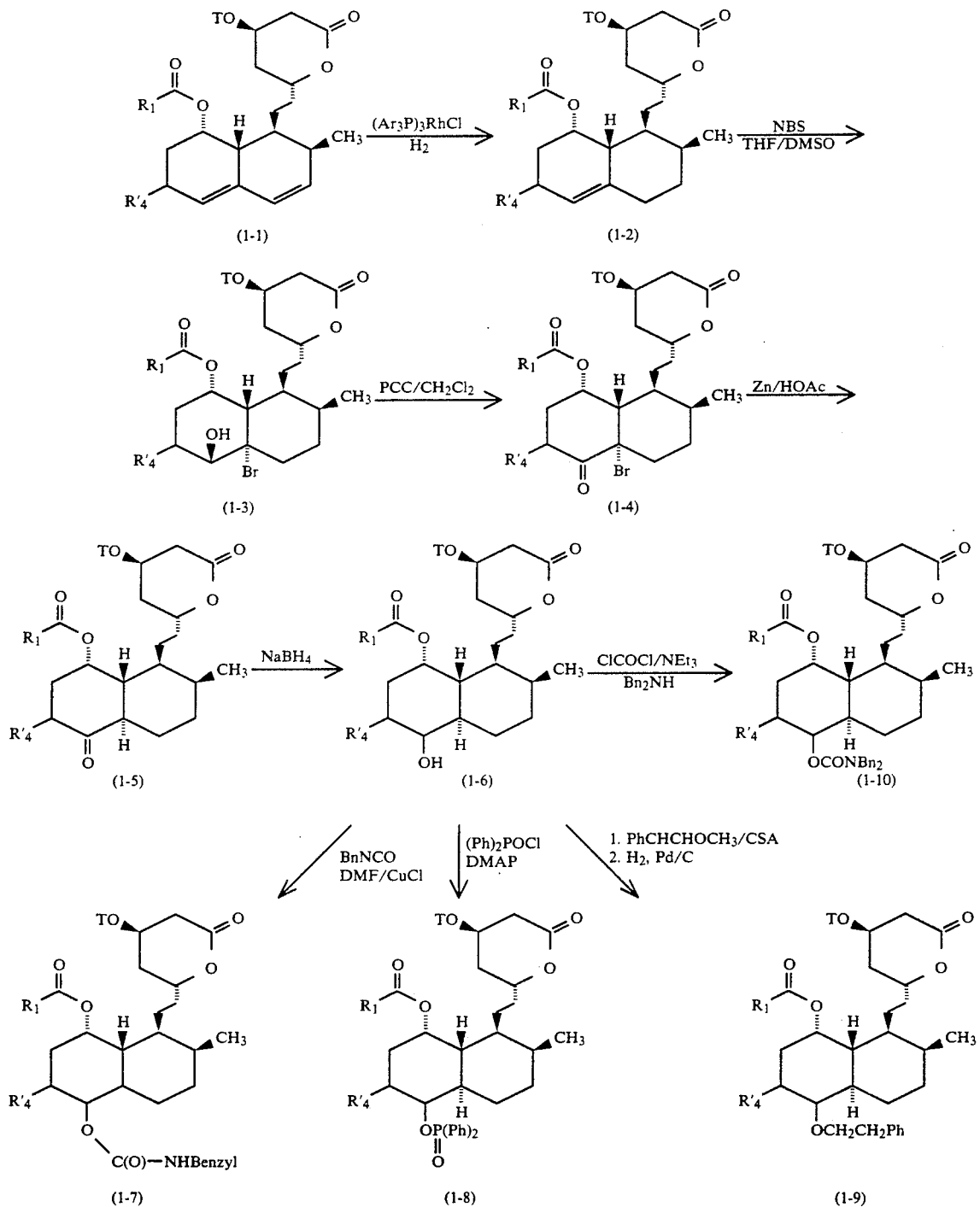

$R_4' = CH_3$ or $CH_2OSi(Me)_2C_4H_9$-t, or H, T is a hydroxy protecting group such as tert-butyldimethylsilyl.

Compound (1-2) is prepared from lovastatin by a reduction of the 3,4 double bond following the procedure detailed in U.S. Pat. No. 4,831,165. Where $R_4$ is 6-hydroxymethyl or a protected hydroxymethyl, the conversion of 6-methyl to 6-hydroxymethyl can be accomplished following the procedure in U.S. Pat. No. 4,940,727. The hydroxyl group in the lactone ring and at the 6-position of the polyhydronaphthyl ring may be protected (TO) using a silyl protecting group such as tert-butyldimethylsilyl, following the procedure in U.S. Pat. No. 4,444,784. Where the acyl moiety is other than 2-methylbutyryl the acyl group of lovastatin may be hydrolyzed and the hydroxyl group reesterified with an appropriate alkanoyl halide following the procedure in U.S. Pat. No. 4,444,784. The alkanoyl halide can be formed by standard transformations such as substitution with an alkyl moiety or other appropriate electrophile at an acidic C-H site on an available starting material.

The monoene (1-2) is converted to the bromohydrin (1-3) using NBS(N-bromosuccimide)/THF/DMSO. The bromohydrin (1-3) is oxidized to the intermediate bromoketone (1-4) with pyridinium chlorochromate (PCC) followed by reductive debromination in THF/acetic acid in the presence of zinc to afford ketone (1-5). Reduction of the ketone (1-5) with NaBH₄ in THF/H₂O gave the epimeric 5-hydroxy derivatives (1-6). The benzyl urethane (1-7) is prepared by treating the alcohol (1-6) with benzyl isocyanate in DMF in the ketone (1-5) which after reprotection of the lactone hydroxy group and treatment with NaBH₄ gives a mixture of the 6-β-methyl-5(S)-hydroxy compound (1-6) and the 6-β-methyl-5(R)-hydroxy compound (1-6).

The methodology of Scheme 2 may be employed where the compounds of Formula (I) contain a double bond in the 3,4 position.

SCHEME 2

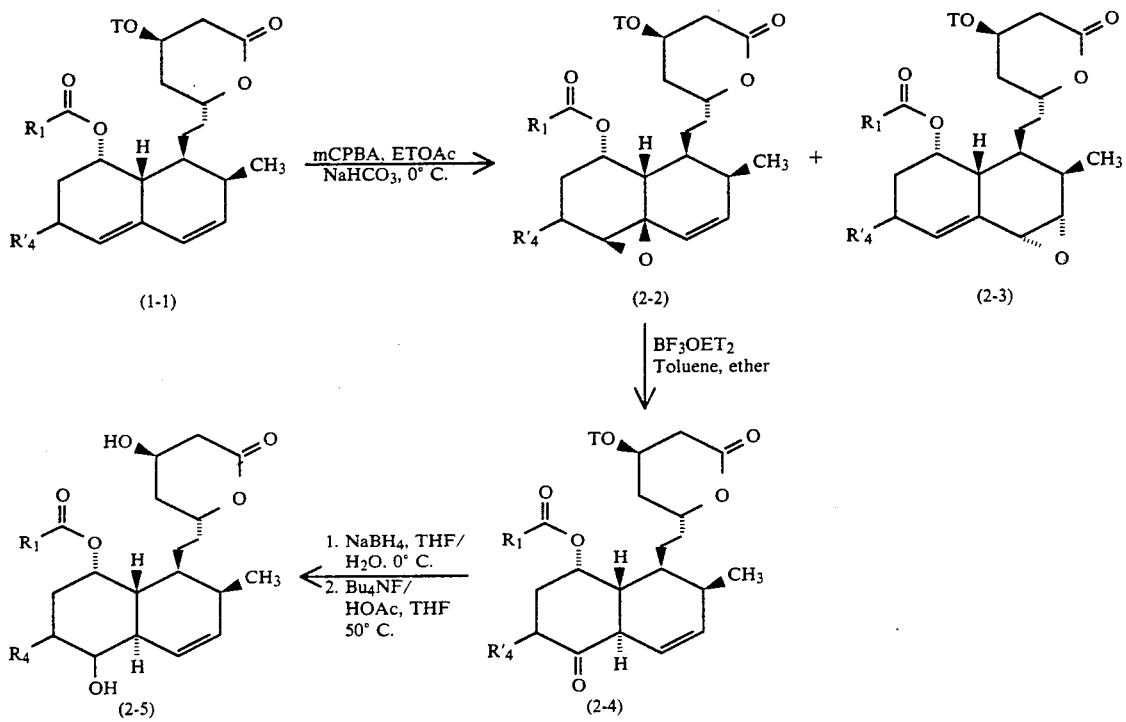

presence of CuCl. The alcohol (1-6) can also be treated with β-methoxy styrene in CH₂Cl₂ in the presence of camphorsulfonic acid (CSA) to yield a Z-enol ether which is reduced with H₂ on 10% Pd/C in ethyl acetate to afford the phenethyl ether (1-9). The phosphinate (1-8) is prepared from the alcohol (1-6) by treatment with diphenylphosphinic chloride and 4-dimethylaminopyridine (DMAP) in CH₂Cl₂. Dibenzylurethanes (1-10) are formed from the initial treatment of alcohol (1-6) with phosgene followed by reaction with dibenzylamine. The 5-alcohol moiety of compound (1-6) can also be converted to the ester, carbonate and ether functionalities by standard chemical transformations.

The 6-hydroxymethyl moiety is converted to a 6-iodomethyl moiety by iodination of the hydroxyl (e.g. iodine, triphenylphosphine, imidazole) followed by substitution or radical mediated coupling with an alkyl or heteroatom moiety which results in the elaboration of CH₂I to R₄. One example of such methodology is the cross-coupling reaction between an alkyl halide and an organometallic reagent (e.g. alkyl iodides with lithium dialkyl copper-Posner, Org. React. 22, 253-400 (1975)).

Copending U.S. Pat. No. 4,940,727 discloses a method of preparing the 6-α-desmethyl 6-β-methyl lovastatin derivative which can be employed as a starting material in the above scheme. Alternatively removal of the silyl protecting T of the 6-α-methyl ketone (1-5) followed by treatment with 1,8-diazabicyclo [5,4,0] undec-7-ene (DBU) results in the 6-β-methyl The hydroxyl protected diene (1-1) is converted to epoxides (2-2) and (2-3) by treatment with m-chloroperoxybenzoic acid at about 0° C. Epoxide (2-2) is then treated with boron trifluoride etherate to form the enone (2-4). The ketone moiety is reduced with NaBH₄ and the lactone hydroxyl deprotected using tetrabutylammonium fluoride to form alcohol (2-5). The 5-alcohol moiety of compound (2-5) can be further treated to form the OR₇ moieties as described in Scheme 1.

Alternatively the double bond may be inserted following the methodology of Scheme 3.

The bromoketone (1-4), formed as an intermediate in Scheme 1, is isolated and dehydrobrominated with pyridine at about 60° C. to form the eneone (3-2). Thiophenol is added to the olefin of (3-2) to form compound (3-3), which then undergoes oxidative elimination with m-chloroperoxybenzoic acid to form compound (3-4). Ketone (3-4) can be deprotected (3-5) and reduced to alcohol (3-6) which can by standard chemistry be converted to any of the OR₇ moieties described above.

Where the reaction conditions of the above noted chemical transformations would be deleterious to the substituents in the 8-acyloxy moiety, the acetoxy group can be employed as a protecting group which after the elaboration of the 5-position can be removed by hydrolysis to give the 8-hydroxy derivative which then can be acylated according to the general procedures described in U.S. Pat. No. 4,661,483.

SCHEME 3

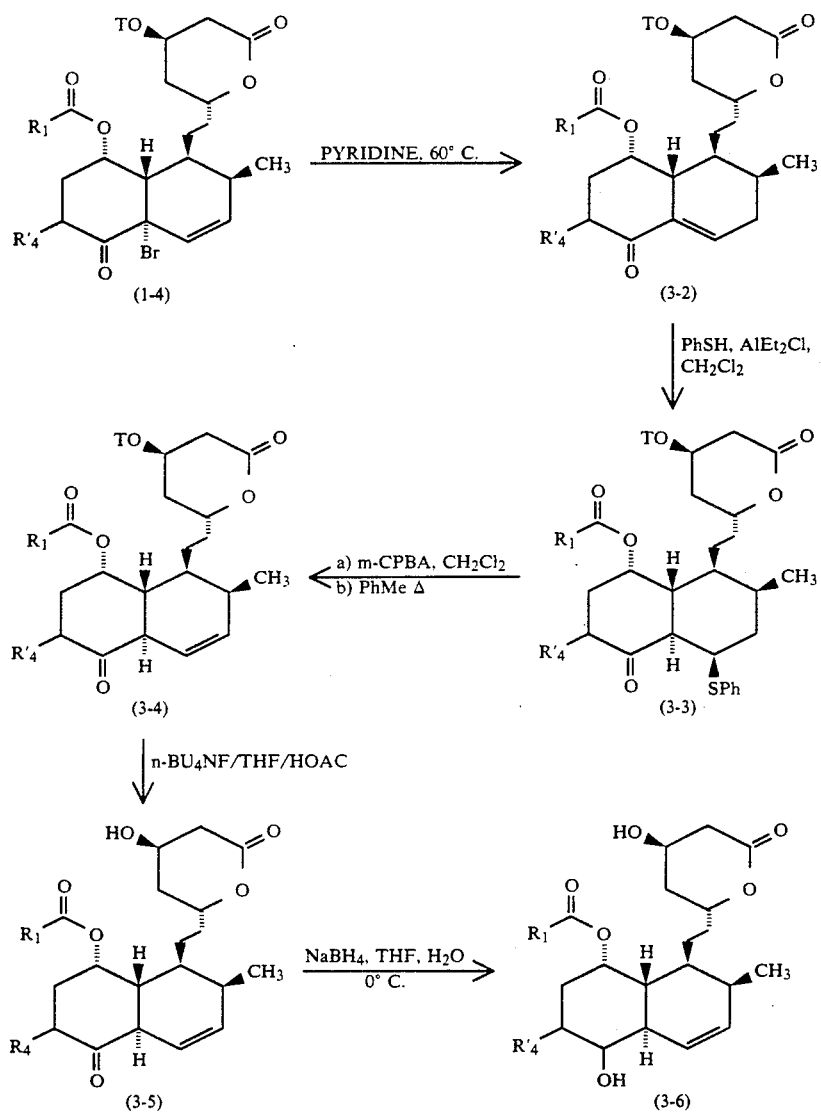

T is a hydroxyl protecting group such as tert-butyldimethylsilyl

Where the product formed by the above described synthetic pathways is not the desired form of that compound, then that product may be subjected to one or more further reactions such as hydrolysis, disilation, salification, esterification, acylation, ammonolysis or lactonization by conventional methods.

Preferred metal salts are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acid salts are basic amino acids, such as arginine, lysine, $\alpha,\beta$-diaminobutyric acid or ornithine.

Preferrred amines to form amine salts include t-octylamine, dibenzylamine, ethylenediamine, morpholine, and tris(hydroxymethyl)aminomethane. Also preferred is ammonia to form the ammonium salt.

Esters are preferably the alkyl esters, such as the methyl, ethyl, propyl, isopropyl, butyl, isobutyl, or pentyl esters, of which the methyl ester is preferred. However, other esters such as phenyl-$C_{1-5}$alkyl, dimethylamino-$C_{1-5}$alkyl, or acetylamino-$C_{1-5}$alkyl may be employed if desired.

Metals salts of the carboxylic acids of formula (II) may be obtained by contacting a hydroxide, carbonate or similar solvent with the carboxylic acid of formula (II). The aqueous solvent employed is preferably water, or it may be a mixture of water with an organic solvent, preferably an alcohol (such as methanol or ethanol), a ketone (such as acetone), an aliphatic hydrocarbon (such as hexane) or an ester (such as ethyl acetate). It is preferred to use a mixture of a hydrophilic organic solvent with water. Such reactions are normally conducted at ambient temperature but they may, if desired, be conducted with heating or cooling.

Amine salts of the carboxylic acids of formula (II) may be obtained by contacting an amine in aqueous solvent with the carboxylic acid of formula (II). suitable aqueous solvents include water and mixtures of water with alcohols (such as methanol or ethanol), ethers (such as diethyl ether and tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion. Alternatively, a metal salt of the carboxylic acid of formula (II) (which may have been obtained as described above) can be dissolved in an aqueous solvent, after which as mineral acid salt (for example the hydrochloride) of the desired amine is added, employing the same reaction conditions as when the amine itself is reacted with the carboxylic acid of formula (II) and the desired product is then obtained by metathesis.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example a mineral acid (such as hydrochloric acid or sulphuric acid), a Lewis acid (for example boron trifluoride) or an acidic ion exchange resin. The solvent employed for this reaction is not critical, provided that it does not adversely affect the reation; suitable solvents include the alcohol itself, benzene, chloroform, ethers and the like. Alternatively, the desired product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. Finally, esters may also be obtained from the lactone of formula (I) by reaction with an appropriate alkoxide in an absolute alkanol. All of the reactions for producing esters are preferably effected at about ambient temperature, but, if required by the nature of the reaction system, the reactions may be conducted with heating or cooling.

Lactones of the carboxylic acids of formula (I) may be obtained by lactonizing the carboxylic acids of formula (II) under ordinary conditions known to one skilled in the art.

The intrinsic HMG-CoA reductase inhibition activity of the claimed compounds is measured in the in vitro protocol published in *J. Med. Chem.*, 28, p. 347–358 (1985).

For estimation of relative inhibitory potencies, compacting (i.e., mevastatin) was assigned a value of 100 and the $IC_{50}$ value of the test compound was compared with that of compactin determined simultaneously in the published in vitro protocol.

Representative of the intrinsic HMG-CoA reductase inhibitory activities of the claimed compounds are the following relative potencies for compounds of formula (I):

| Compound | Relative Potency |
|---|---|
| 6(R)-[2-[8(S)-(2,2-dimethylbutyryloxy)-2(S)-methyl-5(R)-diphenylphosphinyloxy-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one | 300 |
| 6(R)-[2-[8(S)-(2,2-dimethylbutyryloxy)-2(S)-methyl-5(R)-benzylaminocarbonyloxy-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one | 360 |
| 6(R)-[2-[8(S)-(2,2-dimethylbutyryloxy)-2(S)-methyl-5(R)-(1-phenylethyl-2-oxy)-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one | 300 |
| 6(R)-[2-[8(S)-2,2-dimethylbutyryloxy)-2(S)-methyl-5(R)-dibenzylaminocarbonyloxy-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one | 94 |
| 6(R)-[2-[8(S)-(2,2-dimethylbutyryloxy)-2(S)-methyl-5,(R)-hydroxy-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one | 50 |
| 6(R)-[2-[8(S)-(2,2-dimethylbutyryloxy)-2(S)-methyl-5,(R)-hydroxy-6(S)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one | 99.6 |
| 6(R)-[2-[8(S)-(2,2-dimethylbutyryloxy)-2(S)-methyl-5(S)-hydroxy-6(S)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one | 11.1 |
| 6(R)-[2-[8(S)-(2,2-dimethylbutyrloxy)-2(S)-methyl-5-oxo-6(R)-methyl-1,2,3,4,4a(R),6,7,8,8a(R)-nonahydro-naphthyl-1(S)]ethyl]-4(R)-hydroxy-3,4,5,6-tetrahydro-2H-pyran-2-one | 125 |
| 6(R)-[2-[8(S)-(2,2-dimethylbutyryloxy)-2(S)-methyl-5-(R)-hydroxy-6(R)-methyl-1,2,4a(R),5,6,7,8,8a(R)-octahydronaphthyl-1(S)-]ethyl]-4(R)-hydroxy-3,4,5,6-tetrahydro-2H-pyran-2-one. | 100 |

The compounds of this invention are useful as antihypercholesterolemic agents for the treatment of arteriosclerosis, hyperlipidemia, familial hyperchloesterolemia and like diseases in humans. They may be administered orally or parenterally in the form of a capsule, a tablet, an injectable preparation or the like. It is usually desirable to use the oral rout. Doses may be varied, depending on the age, severity, body weight and other conditions of human patients but daily dosage for adults is within a range of from about 10 to 2000 mg (preferably 10 to 100 mg) which may be given in two to four divided doses.

The compounds of this invention may also be coadministered with pharmaceutically acceptable nontoxic cationic polymers capable of binding bile acids in a non-reabsorbable form in the gastrointestinal tract. Examples of such polymers include cholestyramine, coletipol and poly[methyli(3-trimethylaminopropyl)iminotrimethylene dihalide]. The relative amounts of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically-effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims apppended hereto:

EXAMPLE 1

Preparation of
6(R)-[2-[(S)-(2,2-dimethylbutyryloxy)-2(S)-methyl-5(R)-hydroxy-6(R)-methyl-1,2,3,4,4a(R),5,6,7,8,8a(R)-decahydronaphthyl-1(S)]ethyl]4(R)-hydroxy-3,4,5,6-tetrahydro-2H-pyran-2-one (9)

Step 1: Preparationof
6(R)-[2-[8-(2,2dimethylbutyryloxy)-2(S)-methyl-4a(S)-bromo-5(S)-hydroxy-6(R)-methyl-1,2,3,4,5,6,7,8,8a-(R)-nonahydronaphthyl-1(S)]-ethyl]-4(R)-tert-butyldimethylsilylosy-3,4,5,6-tetrahydro-2H-pyran-2-one (2)

To a stirred solution of 6(R)-[2-[8(S)-(2,2-dimethylbutyryloxy)-2(S)-methyl-6methyl-1,2,3,4,6,7,8,8a(R)-octahydronaphthyl-4(R)-tert-butyldimethylsilyloxy-3,4,5,6tetrahydro-2H-pyran-2one (95 mg, 0.23 mmol), DMSO (1.0 mL), THF (0.5 mL), and H₂O (12 μL, 0.7 mmol) at 5° C. was added N-bromosuccinimide (NBS) (61 mg, 0.33 mmol). After 1 hour, the yellow reaction mixture was diluted with ether, washed with H₂O, saturated with NaHCO₃, and brine, dried (MgSO₄), and concentrated. Flash chromatography (silica, 30% EtOAc/hexane) furnished the bromohydrin as a colorless oil.

¹H NMR (CDCk₃) δ5.08(m, 1H), 4.54(m, 1H), 4.26(m, 1H), 4.13(d, J=Hz,1H), 2.63-2.48(m, 2H), 2.35-1.1(m), 1.31(d, J=6 Hz, 3H), 1.13(s, 3H), 1.12(s, 3H), 0.87(s, 9H), 0.8(m, 6H) 0.05(s, 3H), 0.04(s, 3H)

Step 2: Preparation of
6(R)-[2-[8(S)-(2,2-dimethylbutyryloxy)-2(S)-methyl-5-oxo-6(R)-methyl-1,2,3,4,4a(R),6,7,8,8a(R)-nonahydronaphthyl-1(S)]ethyl]-4(R)-tert-butyldimethylsilyloxy-3,4,5,6-tetrahydro-2H-pyran-2-one (3)

To a stirred mixture of compound 2 (2.4 g, 3.8 mmol), 4A sieves (2.5 g), and dry CH₂Cl₂ (19 ml) at 0° C. was added pyridinium chlorochromate (PCC) (3.2 g, 5.2 mmol). After stirring for 30 minutes, the icebath was removed with continued stirring for 30 minutes. The reaction mixture was diluted with ether and filtered through a celite pad into a filtration flask containing acetic acid (0.8 mL, 14.0 mmol). Concnetration at 10° C. gave the crude bromoketone which was reduced immediately. The crude bromoketone was dissolved in THF/FOAc (38 mL) followed by treatment with zinc (0.74 g, 11.4 mmol) at ambient temperature. After 1.0 hour of vigorous stirring, the reaction mixture was diluted with ether and the excess zinc removed by filtration. The filtrate was washed with H₂O and brine, dried (MgSO₄), and concentrated. Flash chromatography (silica, 15% EtOAc/hexanes) gave compound 3 as a solid (m.p. 147°-148° C.).

¹H NMR (CDCl₃) δ5.31(m, 1H), 4.60(m, 1H), 4.29(m, 1H), 2.58(m, 2H), 2.24-1.20(m), 1.24(d, J=7Hz, 3H), 1.88(s, 3H), 1.17(s, 3H), 0.89(s, 9H), 0.87(d, J=7 Hz, 3H), 0.83(t, J=7H), 0.06(s, 6H)

Step 3: Preparation of
6(R)-[2-[8(S)-(2,2-dimethylbutyryloxy)-2(S)-methyl-5(R)-hydroxy-6(R)-methyl-1,2,3,4,a(R),5,6,7,8,8a(R)-decahydromaphthyl-1(S)]ethyl]-4(R)-tert-butyldimethylsilyloxy-3,4,5,6tetrahydro-2H-pyran-2-one (4)

To a stirred solution of compound 3 (320 mg, 0.58 mmol), THF (2.6 mL), and H₂O (0.3 mL) at 0° C. was added NaBH₄ (66 mg, 1.7 mmol). After 35 minutes, the reaction mixture was diluted with ethyl acetate, washed with H₂0 (2X) and brine, dried (MgSO₄), and concentrated. Flash chromatography (silica, 20% ethyl acetate/hexane) gave compound 4 as a colorless oil.

¹H NMR (CDCl₃) δ5.06(m, 1H), 4.60(m, 1H), 4.14(m, 1H), 3.45(dd, J=10 and 5Hz, 1H), 2.56(m, 2H), 2.15-1.15(m), 1.17(s, 3H), 1.16 (s, 3H), 1.07(d, J=7Hz, 3H), 0.88 (s, 9H), 0.88(t, J=7Hz, 3H), 0.86(d, J=7Hz, 3H), 0.08(s, 3H), 0.88(s, 3H)

Step 4: Preparation of
6(R)-[2-[8(s)-(2,2-dimethylbutyryloxy)-2(S)-methyl-5(R)-hydroxy-6(R)-methyl-1,2,3,4,4a(R),6,7,8,8a(R)-decahydromaphthyl-1(S)]ethyl]-4(R)-hydroxy-3,4,5,6-tetrahydro-2H-pyran-2-one (9)

To a stirred solution of compound 4 (98 mg, 0.18 mmol), THF (530 μL), and HOAc (41 μL, 0.71 mmol) was added tetrabutylammonium fluoride (1M THF, 530 μL, 0.53 mmol) at ambient temperature. After 20 hours, the reaction mixture was diluted with ethyl acetate, washed with H₂O and brine, dried (MgSO₄), and concentrated. Flash chromatography (silica, 60% EtOAc/hexane) gave compound (9) as a crystalline solid. mp=142°-143° C.

¹H NMR (CDCl₃) δ5.05(m, 1H), 4.54(m, 1H), 4.31(m, 1H), 3.42(dd, J=10 and 5Hz, 1H), 2.69(dd, J=17 and 5Hz, 1H), 2.57(dd, J=17 and 4Hz, 1H), 2.12-1.10(m), 1.17(s, 3H), 1.16(s, 3H), 1.06(d, J=7Hz, 3H), 0.82(t, J=7Hz, 3H), 0.79(d, J=7Hz, 3H)

Elemental Anal. C₂₅H₄₂O₆·0.5H₂O: Calc'd: C, 67.08; H, 9.68; Found: C, 66.84; H, 9.31.

EXAMPLE 2

Preparation of
6(R)-[2-[8(S)-(2,2-dimethylbutyryloxy)-2(S)-methyl-5(R)-benzylaminocarboxy-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one (11)

Step 1: Preparation of
6(R)-[2-[8(S)-(2,2-dimethylbutyryloxy)-2(S)-methyl-4a(S)-bromo-5(S)-hydroxy-6(R)-methyl-1,2,3,4,5,6,7,8,8a-(R)-nonahydronaphthyl-1(S)]ethyl]-4(R)-tert-butyldimethylsilyloxy-3,4,5,6-tetrahydro-2H-pyran-2-one (2)

To a stirred solution of 6(R)-[2-[8(S)-)2,2-dimethylbutyryloxy)-2(S)-methyl-6(R)-methyl-1,2,3,4,6,7,8,8a(R)-octahydronaphthyl-1(S)]ethyl]-4(R)-tert-butyldimethylsilyloxy-3,4,5,6-tetrahydro-2H-pyran-2-one (95 mg, 0.23 mmol) DMSO (1.0 mL), THF (0.5 mL), and H₂O (12 μL, 0.7 mmol) at 5° C. was added N-bromosucciinimide (NBS) (61 mg, 0.33 mmol). After 1 hour, the yellow reaction mixture was diluted with ether, washed with H₂O, saturated with NaHCO₃, and brine, dried (MgSO₄), and concentrated. Flash chromatography (silica, 30% EtOAc/hexane) furnished the bromohydrin as a colorless oil.

¹H NMR (CDCl₃) δ5.08(m, 1H), 4.54(m, 1H), 4.26(m, 1H), 4.13(d, J=3Hz, 1H), 2.63-2.48(m, 2H), 2.35-1.1(m), 1.31(d, J=6Hz, 3H), 1.13(s, 3H), 1.12(s, 3H), 0.87(s, 9H), 0.8(m, 6H), 0.05(s, 3H), 0.04(s, 3H)

Step 2: Preparation of 6(R)-[2-[8(S)-(2,2-dimethylbutyryloy)-2(S)-methyl-5-oxo-6(R)-methyl-1,2,3,4,4a(R),6,7,8,8a(R)-nonahydronaphthyl-1(S)]ethyl]-4(R)-tert-butyldimethylsilyloxy-3,4,5,6-tetrahydro-2H-pyran-2-one (3)

To a stirred mixture of compound 2 (2.4 g, 3.8 mmol), 4A sieves (2.5 g), and dry CH₂Cl₂ (19 ml) at 0° C. was added pyridinium chlorochromate (PCC) (3.2 g, 5.2 mmol). After stirring for 30 minutes, the icebath was removed with continued stirring for 30 minutes. The reaction mixture was diluted with ether and filtered through a celite pad into a filtration flask containing acetic acid (0.8 mL, 14.0 mmol). Concentration at 10° C. gave the crude bromoketone which was reduced immediately. The crude bromoketone was dissolved in THF/HOAc (38 mL) followed by treatment with zinc (0.74 g, 11.4 mmol) at ambient temperature. After 1.0 hour of vigorous stirring, the reaction mixture was diluted with ether and the excess zinc removed by filtration. The filtrate was washed with H₂O and brine, dried (MgSO₄), and concentrated. Flash chromatography (silica, 15% EtOAc/hexanes) gave compound 3 as a solid. (m.p. 147°-148° C.)

¹H NMR (CDCl₃) δ5.31(m, 1H), 4.60(m, 1H), 4.29(m, 1H), 2.58(m, 2H), 2.24-1.20(m), 1.24(d, J=7Hz, 3H), 1.88(s, 3H), 1.17(s, 3H), 0.89(s, 9H), 0.87(d, J=7Hz, 3H), 0.83(t, J=7Hz, 3H), 0.06(s, 6H)

Step 3: Preparation of 6(R)-[2-[8(S)-(2,2-dimethylbutyryloxy)-2(S)-methyl-5(R)-hydroxy-6(R)-methyl-1,2,3,4,4a(R),5,6,7,8,8a(R)-decahydronaphthyl-1(S)]ethyl]-4(R)-tert-butyldimethylsilyloxy-3,4,5,6-tetrahydro-2H-pyran-2-one (4)

To a stirred solution of compound 3 (320 mg, 0.58 mmol), THF (2.6 mL), and H₂O (0.3 mL) at 0° C. was added NaBH₄ (66 mg, 1.7 mmol). After 35 minutes, the reaction mixture was diluted with ethyl acetate, washed with H₂O (2×) and brine, dried (MgSO₄), and concentrated. Flash chromatography (silica, 20% ethyl acetate/hexane) gave compound 4 as a colorless oil.

¹H NMR (CDCl₃) δ5.06(m, 1H), 4.60(m, 1H), 4.14(m, 1H), 3.45(dd, J=10 and 5Hz, 1H), 2.56(m, 2H), 2.15-1.15(m), 1.17(s, 3H), 1.16(s, 3H), 1.07(d, J=7Hz, 3H), 0.88(s, 9H), 0.88(t, J=7Hz, 3H), 0.86(d, J=7Hz, 3H), 0.08(s, 3H), 0.08(s, 3H)

Step 4: Preparation of 6(R)-[2-[8(S)-(2,2-dimethylbutyryloxy)-2(S)-methyl-5(R)-benzylaminocarbonyloxy-6(R)-methyl-1,2,3,4,4a(R),5,6,7,8,,8a(R)-decahydronaphthyl-1(S)]ethyl]-4(R)-tert-butyldimethylsilyloxy-3,4,5,7-tetrahydro-2H-pyran-2-one (10)

To a mixture of compound 4 (227 mg, 0.41 mmol), degassed DMF (2.0 mL), and CuCl (41 mg, 0.41 mmol) at 25° C. was added benzyl isocyanate (82 mg, 0.62 mmol). After 1 hour, the dark green mixture was diluted with ether, washed with H₂O and brine, dried (MgSO₄), and concentrated. Flash chromatography (silica, 20% EtOAc/hexane) furnished compound 10 as a colorless oil.

¹H NMR (CDCl₃) δ7.30(m, 5H), 5.06(m, 1H), 4.93(m, 1H), 4.61(dd, J=10 and 5Hz, 1H), 4.37(d, J=6Hz, 2H), 4.25(m, 1H), 2.55(m, 2H), 2.27(m, 1H), 2.00-1.10(m), 1.14(s, 3H), 1.13(s, 3H), 0.86(s, 9H), 0.80(m, 9H), 0.06(s, 6H).

Step 5: Preparation of 6(R)-[2-[8(S)-(2,2-dimethylbutyryloxy)-2(S)-methyl-5(R)-benzylaminocarbonyloxy-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one (11)

Utilizing the same procedure of Example 1, Step 4, the compound 10 (80 mg, 0.11 mmol) was converted to the desired compound (11) which was an amorphous solid.

¹H NMR (CDCl₃) δ7.30(m, 5H), 5.08(m, 1H), 5.02(t, J=6Hz, 1H), 4.59(dd, J=10 and 5Hz, 1H), 4.54(m, 1H), 4.34(d, J=6Hz, 2H), 4.30(m, 1H), 3.03(bs, 1H), 2.69(dd, J=18 and 5Hz, 1H), 2.58(dd, J=18 and 4Hz, 1H), 2.26(m, 1H), 2.00-1.10(m), 1.14(s, 3H), 1.13(s, 3H), 0.82(t, J=7Hz, 3H), 0.78(d, J=7Hz, 3H).

Elemental Anal. C₃₃H₄₉O₇N·1.5H₂O Calc'd: C, 66.20; H, 8.75 N, 2.34; Found: C, 65.86; H, 8.99 N, 2.03.

EXAMPLE 3

Preparation of 6(R)-[2-[8(S)-(2,2-diimethylbutyryloxy)-2(S)-methyl-5(R)-hydroxy-6(S)-methyl-1,2,3,4,4a(R),6,7,8,8a(R)-decahydronaphthyl-1(S)]ethyl]-4(R)-hydroxy-3,4,5,6-tetrahydro-2H-pyran-2-one (14) and 6(R)-[2-[8(S)-(2,2-dimethylbutyryloxy)-2(S)-methyl-5(S)-hydroxy-6(S)-methyl-1,2,3,4,4a(R),6,7,8,8a(R)decahydronaphthyl-1(S)]ethyl]-4(R)-hydroxy-3,4,5,6-tetrahydro-2H-pyran-2-one (15)

Example 1, Steps 1-2 were repeated but substituting tert-butyldiphenylsilyl as the hydroxyl protecting group.

Step 3: Preparation of 6(R)-[2-[8(S)-(2,2-dimethylbutyryloxy)-2(S)-methyl-5-oxo-6(R)-methyl-1,2,3,4,4a(R),6,7,8,8a(R)-nonahydronaphthyl-1(S)]ethyl]-4(R)-hydroxy-3,4,5,6-tetrahydro-2H-pyran-2-one (12)

To a stirred solution of 6(R)-[2-[8(S)-(2,2-dimethylbutyryoxy)-2(S)-methyl-5-oxo-6(R)-methyl-1,2,3,4,4a(R), 6,7,8,8a(R)-nonahydronaphthyl-1(S)]ethyl]-4(R)-tert-butyldiphenylsilyloxy-3,4,5,6-tetrahydro-2H-pyran-2-one (345 mg, 0.63 mmol) and CH₂Cl₂ (3.1 mL) at 0° C. was added HF·pyridine (0.19 g). After 1 hour, the reaction mixture was diluted with ethyl acetate, washed carefully with saturated NaHCO₃ and brine, dried (MgSO₄), and concentrated. Flash chromatography (silica, 50% ethyl acetate/hexane) furnished compound 12 as a colorless solid.
mp=159°-160° C.

¹H NMR (CDCl₃) δ5.36(m, 1H), 4.63(m, 1H), 4.40(m, 1H), 2.78(dd, J=18 and 5Hz, 1H), 2.60(m, 2H), 2.20(m, 1H), 2.05-1.15(m), 1.26(d, J=7Hz, 3H), 1.21(s, 3H), 1.20(s, 3H), 0.88(t, J=7Hz, 3H), 0.85(d, J=7Hz, 3H)

Step 4: Preparation of 6(R)-[2-[8(S)-(2,2-dimethylbutyryloxy)-2(S)-methyl-5-oxo-6(S)-methyl-1,2,3,4,4a(R),6,7,8,8a(R)-nonahydronaphthyl-1(S)]ethyl-4(R)-hydroxy-3,4,5,6-tetrahydro-2H-pyran-2-one (13)

A stirred solution of compound 12 (150 mg, 0.34 mmol), 1,8-diazabicyclo[5,4,0]undec-7-ene (DBU) (52 μL, 0.34 mmol), and dry toluene was heated at 80° C. for 3 hours. The cooled reaction mixture was concentrated and the residue subjected to flash chromatography (silica, 50% ethyl acetate/hexane) to give the desired compound 13 as a crystalline solid, (m.p. 133°-134° C.).

¹H NMR (CDEDCl₃) δ5.28(m, 1H), 4.48(m, 1H), 2.74(dd, J=18 and 5Hz, 1H), 2.62(m, 2H), 2.47(ddd, J=9, 9, and 3Hz, 1H), 2.33(m, 1H), 2.00-1.10(m), 1.23(s, 3H), 1.22(s, 3H), 0.98(d, J=7Hz, 3H), 0.87(t, J=7Hz, 3H), 0.80(d, J=7Hz, 3H)

Step 5: Preparation of
6(R)-[2-[8(S)-(2,2-dimethylbutyryloxy)-2(S)-methyl-5(R)-hydroxy-6(S)-methyl-1,2,3,4,4anR),
6,7,8,8a(R)-decahydronaphthyl-1(S)]ethyl]-4(R)-hydroxy-3,4,5,6-tetrahydro-2H-pyran-2one (14) and 6(R)-[2-[8(S)-(2,2-dimethylbutyryloxy)-2(S)-methyl-5(S)-hydroxy-6(S)-methyl-1,2,3,4,4a-(R),
6,7,8,8a(R)-decahydronaphtyl-1(S)]-ethyl]-4(R)-hydroxy-3,4,5,6-tetrahydro-2H-pyran-2-one (15)

To a stirred solution of compound 13 (68 mg, 0.15 mmol), THF (1.4mL), and H₂O (0.15 mL) at 0° C. was added NaBH₄ (11 mg, 0.30 mmol). After 15 minutes, the reaction mixture was diluted with ethyl acetate, washed with H₂O and brine, dried (MgSO₄) and concentrated. Flash chromatography (silica, 15% acetone/benzene) gave a faster moving compound 14 and a slower moving compound 15 as amorphous solids.

¹H NMR of compound (14) (CDCl₃)δ5.08(m, 1H), 4.57(m, 1H), 4.367, 1H), 2.86(ddd, J=10, 5, and 5Hz, 1H), 2.74(dd, J=18 and 5Hz, 1H), 2.61(m, 1H), 2.05-1.15(m), 1.17(s, 6H), 1.00(d, J=7Hz. 3H), 0.85(t, J=7Hz, 3H), 0.83(d, J=PHz, 3H)

Elemental Anal. C₂₅H₄₂O₆ Calc'd: C, 68.46; H, 9.65; Found: C, 68.17; H, 9.50.

¹H NMR (CDCl₃) of compound (15)δ5.14(m, 1 H), 4.59(m, 1H), 4.36(m, 1H), 3.53(bs, 1 H), 2.74(dd, J=18 and 5Hz, 1H), 2.60(m, 1H), 2.20(d, J=3Hz, 1H), 2.00-1.20nm), 1.17ns, 3H), 1.16(s, 3 H), 0.95(d, J=7 Hz, 3 H), 0.85(t, J=7Hz, 3 H), 0.84nd, J=7Hz, 3 H)

Elemental Anal. C₂₅H₄₂O₆ Calc'd: C, 68.46; H, 9.65; Found: C, 68.09; H, 9.18.

EXAMPLE 4

Preparation of
6(R)-[2-[8(S)-2,2-dimethylbutyryloxy)-2(S)-methyl-5(R)-(1-phenylethyl-2oxy)-6(R)-methyl-1,2,3,4,4a(R),5,6,7,8,8a(R)-decahydronaphthyl-1(S)]-ethyl]-4(R)-hydroxy-3,4,5,6-tetrahydro-2H-pyran-2-one (18)

Example 1, Steps 1-3 were repeated but substituting tert-butyldiphenylsilyl as the hydroxy protecting group.

Step 4:
6(R)-[2-[8(S)-(2,2-dimethylbutyryloxy)-2(S)-methyl-5(R)-(1-phenylethylen-2-oxy)-6(R)-methyl-1,2,3,4,4a(R)-methyl-1,2,3,4,4a (R),
5,6,7,8,8a(R)-decahydronaphtyl-1(S)]ethyl]-4(R)-tert-butyldiphenylsilyloxy-3,4,5,6-tetrahydro-2H-pyran-2-one (16)

To a stirred solution of 6(R)-[2-[8(S)-(2,2-dimethylbutyryloxy)-2(S)-methyl-5(R)-hydroxy-6(R)-methyl-1,2,3,4,4a(R),5,6,7,8,8anR)-decahydronaphthyl-1(S)]ethyl]-4(R)-tert-butyldiphenylsilyoxy-3,4,5,6-tetrahydro-2H-pyran-2one (270 mg, 0.40 mmol), β-methoxystyrene (165 μL, 1.2 mmole and dry CH₂Cl₂ (4mL) at 0° C. was added (±)-camphorsulfonic acid (23 mg, 0.10 mmol). After 15 minutes, the cooling bath was removed and stirring continued for 3 hours. The reaction was quenched with NEt₃ (195 μL, 1.2 mmol) concentrated, and the residue subjected to flash chromatography (silica, 15% EtOAc/hexane) to afford compound 16 as a colorless foam.

¹H NMR (CdCl₃)δ7.68-7.20(m, 15H), 6.23(d, J=7Hz, 1H), 5.20(d, J=7Hz, 1H), 5.09(m, 1 H), 4.67(m, 1 H), 4.27(m, 1H), 3.56(dd, J=10 and 5 Hz, 1H), 2.57(m, 1 H), 2.57(m, 1 H), 2.43(dd, J=18 and 4Hz, 1 H), 2.26(m, 1H), 2.10-1.10(m), 1.17(s, 3H), 1.16ns, 3H), 1.08(s, 9 H), 1.08ns, 9 H), 0.86(t, J=7Hz, 3H), 0.84nd, J=7Hz, 3H)

Step 5: Preparation of
6(R)-[2-[8(S)-2,2-dimethylbutyryloxy)-2-(S)-methyl-5(R)-(1-phenylethyl-2-oxy)-6(R)-methyl-1,2,3,4,4a(R),
5,6,7,8a(R)-decahydronaphthyl-1(S)]ethyl]-4(R)-tetrabutyldiphenylsilyloxy-3,4,5,6-tetrahydro-2H-pyran-2-one (17).

A mixture of compound 16 (150 mg. 0.19 mmol) 10% pd/C (30 mg), and ethyl acetate (5.0 ml) was stirred at 25° c. under a hydrogen atmosphere (1 atm) for 8.0 hours. The reaction mixture was filtered through a celite pad and concentrated. Flash chromatography (silica, 15% ethyl acetate/hexane) gave compound 17 as a colorless oil.

¹H NMR (CDCl₃) δ7.65¼7.20(m, 15 H), 5.00(m, 1 H), 4.66 (m, 1 H), 4.23(m, 1 H), 3.78(m, 1 H), 3.46 (m, 1 H), 3.02(dd, J=10 and 5 Hz, 1 H), 2.88(ddd, J=7,7, and 3 Hz, 2 H), 2.56(m, 1H), 2.41(dd, J=18 and 4 Hz, 1 H), 2.22(m, 1H), 2.05-1.10(m), 1.14(s, 3H), 1.08(s, 9H), 0.98nd, J=7 Hz, 3 H, 0.82(t, J=7 Hz, 3 H), 0.79(d, J=7 Hz, 3 H).

Step 6: Preparation of
6(R)-[2-[8(S)-(2,2-dimethylbutyryloxy)-2(S)-methyl-5(R)-(1-phenylethyl-2oxy)-6(R)-methyl-1,2,3,4,4a(R),
4,6,7,8,8a(R)-decahydronaphthyl-1(S)]ethyl]-4(R)-hydroxy-3,4,5,6-tetrahydro-2H-pyran-2-one (18)

Utilizing the procedure of Example 1, Step 4 the compound 17 (39 mg, 50 mmol) was converted to the desired compound 18 which was a colorless oil.

¹H NMR (CDCl₃)δ7.25(m, 5H), 5.05nm, 1H), 4.55(m, 1 H), 4.32nm, 1 H), 3.73(m, 1 H), 3.47 (m, 1 H), 3.01 (dd, J=10 and 5 hz, 1 H), 2.88 (m, 2 H), 2.71(dd, J=18 and 5 Hz, 1 H), 2.59 (dd, J=18 and 4 Hz, 1 H), 2.22(m, 2 H), 2.00-1.10(m), 1.14(s, 3H), 1.13(s, 3 H), 0.99 (d, J=7 Hz, 3 H), 0.82(t, J=7Hz, 3 H), 0.78nd, J=7 Hz, 3 H).

Elemental Analysis: C₃₃H₅₀O₆·0.25 H₂O Calc'dd C, 72.43; H, 9.32; Found: C, 72.53; H, 9.32.

EXAMPLE 5

Preparation of
6(R)-[2]8(S)-(2,2-dimethylbutyryloxyl)-2(S)-methyl-5(R)-dibenzylaminocarbonyloxy-6(R)-methyl-1,2,3,4,4a(R)-decahydronaphthyl-1(S)]ethyl]-4(R)-hydroxy-3,4,5,6-tetrahydro-2h-pyran-2-one (20)

Example 1, Steps 1-3 were repeated but substituting tert-butyldiphenylsilyl as the hydroxy protecting group.

Step 4: Preparation of 6(R)-[2-[8(S)-(2,2-dimethylbutryloxy)-2(S)-methyl-5(R)-dibenzylaminocarbonyloxy-6(R)-methyl-1,2,3,4,4a(R),5,6,7,8,8a(R)-decahydronaphthyl-1(S)ethyl]-4(R) tert-butyldiphenylsilyloxy-3,4,5,6-tetrahydro-2 H-pyran-2-one (19).

A solution of 6(R)-[2-[8(S)-(2,2-dimethylbutryloxy)-2(S)-methyl-5(R)-hydroxy-6(R)-methyl-1,2,3,4,4a(R),5,6,7,8,8a(R)decahydronaphthyl-1(S)ethyl]-4(R)-tert-butyldiphenylsilyloxy-3,4,5,6-tetrahydro-2H-pyran-2one (25 mg, 37 mmol), triethylamine (21 μL, 0.15 mmol), and dry CH$_2$Cl$_2$ (200 μL) was added dropwise to a stirred solution of phosgene (20% in toluene, 67 μL, 0.15 mmol) and CH$_2$Cl$_2$ (600 μL) at 0° c. After 5 minutes the cooling bath was removed and the reaction mixture stirred for 20 minutes. Concentration is situ followed by sequential addition of CH$_2$CL$_2$ (400 μL) and dibenzylamine (8 μL, 41 mmol) at ambient temperature, resulted in a heterogeneous mixture. After 15 minutes the reaction mixture was diluted with ether, washed with H$_2$O and brine, dried (MgSO$_4$), and concentrated. Flash chromatography (silica, 15-20% ethyl acetate/hexane) gave compound 19 as an oil.

$^1$H NMR (CDCl$_3$)δ7.63-7.26(m, 20 H), 5.12(m, 1 H), 4.75 (dd, J=10 and 5 Hz, 1 H), 4.60nm, 1 H), 4.40 (m, 2 H), 4.33nm, 1 H), 2.60nm, 2 H), 2.20-1.10(m), 1.17(s, 3 H), 1.16(s, 3 H), 1.07(s, 9 H), 1.00 (d, J=7 Hz, 3 H), 0.80(m, 6 H).

Step 5: Preparation of 6(R)-[2-[8(Se-(2,2-dimethylbutryloxyl)-2(S)-methyl-5(R)-dibenzylaminocarbonyloxy-6(R)-methyl-1,2,3,4,4a(R), 5,6,7,8,8a(R)-decahydronaphthyl-1(S)]ethyl]-4(R)-hydroxy-3,4,5,6-tetrahydro-2 H-pyran-2-one (20).

Compound 19 (72 mg, 79 mmol) was dissolved in a premixed solution of tetrabutylammonium fluoride (1M in THF, 300 μL, 0.3 mmol), HOAc (20 mL, 0.3 mmol), and THF (300 μL) followed by heating at 50° C. for 1.0 hour. The cooled reaction mixture was diluted with ether, washed with H$_2$O and brine, dried (MgSO$_4$), and concentrated. Flash chromatography (silica, 60% EtOAc/hexane) gave compound 20 as a colorless foam.

$^1$H NMR (CDCl$_3$e δ7.37-7.18(m, 10 H), 4.75(dd, J=10 and 5 Hz, 1 H), 4.59(m, 1 H), 4.47(m, 3 H), 4.34nm, 1 H), 2.72(dd, J=18 and 5 Hz, 1 H), 2.61ndd, J=18 and 3 Hz, 1 H), 2.32(m, 1H), 2.00-1.10(m), 1.16(s, 3 H), 1.15(s, 3 H), 1.00(d, J=7 Hz, 3 H), 0.84(t, J=7 Hz, 3 H), 0.83(d, J=7 Hz, 3 H).

Elemental Analysis: C$_{40}$H$_{55}$O$_7$N·0.5 H$_2$O Cald'd: C, 71.61; H, 8.41; N, 2.09; Found: C, 71.66; H, 8.31; N, 2.04.

EXAMPLE 6

Preparation of 6(R)-[2-[8(S)-(2,2-dimethylbutryloxy)-2(S)-methyl-5(R)-diphenylphosphinyloxy-6(R)-methyl-1,2,3,4,4a(R),5,6,7,8,8a(R)-decahydronaphthyl-1(S)}ethyl]-4(R)-hydroxy-3,4,5,6-tetrahydro-2H-pyran-2-one (21)

Example 1, Steps 1-3 were repeated but substituting tert-butyldiphenylsilyl as the hydroxyl protecting group.

Step 4: Preparation of 6(R)-[2-[8(S)-(2,2-dimethylbutryloxy)-2(S)-methyl-5(R)-diphenylphosphinyloxy-6(R)-methyl-1,2,3,4,4a(R),5,6,7,8,8a(R)-decahydronaphthyl-1(S)ethyl]-4(R)-tert-butyldiphenylsilyloxy-3,4,5,6,-tetrahydro-2H-pyran-2-one (21).

To a stirred solution of 6(R)-[2-[8(S)-(2,2-dimethylbutryloxy)-2(S)-methyl-5(R)-hydroxy-6(R)-methyl-1,2,3,4,4a(R),5,6,7,8,8a(R)-decahydronaphthyl-1(S)ethyl]-4(R)-tert-butylidphenylsilyloxy-3,4,5,6-tetrahydro-2H-pyran-2-one (59 mg, 87 μmol) N,N-dimethyl aminopyridine (DMAP) (43 mg, 0.35 mmol), and CH$_2$Cl$_2$ (0.44 mL) at ambient temperature was added diphenyl phosphinic chloride (33 μL, 0.17 mmol). After 20 minutes the reaction mixture was diluted with ether, washed with H$_2$O and brine, dried (MgSO$_4$), and concentrated. Flash chromatography (silica, 45% EtOAc/hexane) gave compound 21 as an oil.

$^1$H NMR (CDCl$_3$) δ7.85-7.25(m, 20H), 4.98(m, 1H), 4.64(m, 1H), 4.28(m, 2H), 2.55(m, 1H), 2.39(dd, J=18 and 4 Hz, 1H), 2.05-1.10(m), 1.14(s, 3H), 1.13(s, 3H), 1.12(d, J=7 Hz, 3H), 1.03(s, 9H), 0.81(t, J=7 Hz, 3H), 0.73(d, J=7 Hz, 3H).

Step 5: Preparation of 6(R)-[2-[8(S)-(2,2-dimethylbutryloxy)-2(S)-methyl-5(R)-diphenylphosphinyloxy-6(R)-methyl-1,2,3,4,4a(R),5,6,7,8,8a(R)-decahydronaphthyl-1(S)ethyl]-4-(R)-hydroxy-3,4,5,6-tetrahydro-2H-pyran-2one (22)

To a stirred solution of compound 21 (64 mg 73 μmol), THF (0.3 mL), and HOAc (17 μL, 0.3 mmol) was added tetrabutylammonium fluoride (1M in THF, 300 μL, 0.3 mmol) followed by heating at 50° C. After 3.0 hours the cooled reaction mixture was diluted with ether, washed with H$_2$O and brine, dried (MgSO$_4$), and concentrated. Flash chromatography (silica, 80% ethyl acetate/hexane) gave compound 22 as a colorless oil.

$^1$H NMR (CDCl$_3$) δ7.80(m, 6H), 5.01(m, 1H), 4.54(m, 1H), 4.30(m, 1H), 4.27(m, 1H), 2.62(m, 3H), 2.10-1.10(m), 1.14(s, 3H), 1.13(s, 3H), 1.12 (d, J=7 Hz, 3H), 0.82(t, J=7 Hz, 3H), 0.73(d, J=7 Hz, 3H).

Elemental Analysis: C$_{37}$H$_{51}$O$_7$P·0.5 H$_2$O Cald'd: C, 68.60; H, 8.09; Found: C, 68.69; H, 8.03.

EXAMPLE 7

6(R)-[2-[8(S)-(2,2-dimethylbutryloxy)-2(S)-methyl-5-(R)-hydroxy-6(R)-methyl-1,2,4a(R),5,6,7,8,8a(R)-octahydronaphthyl-1(S)]ethyl]-4(R)-hydroxy-3,4,5,6-tetrahydro-2H-pyran-2-one; and the corresponding ring opened dihydroxy acids and esters thereof.

Step 1: Preparation of 6(R)-[2-[8(S)-(2,2-dimethylbutryloxy)-2(S)-methyl-6(R)-methyl-1,2,6,7,8,8a(R)-hexahydronaphthyl-1(S)ethyl]-4(R)-tert-butyldiphenylsilyloxy-3,4,5,6-tetrahydro-2H-pyran-2-one (23).

To a stirred solution of Simvastatin (20.0 g, 48 mmol), imidazole (8.2 g, 0.12 mol), and dry DMF (100 mL) at 25° C. was added tert-butyldiphenylsilylchloride (13.0 mL, 50 mmol). After stirring at 25° C. for 18 hours the reaction mixture was diluted with pet, ether, washed with H$_2$O (2×) and brine, dried (MgSO$_4$), and concentrated to furnish (23) as a colorless oil.

TLC R$_f$=0.75 (silica, 30% ethyl acetate/hexanes); $^1$H NMR (CDCl$_3$) δ7.63 (m, 4H), 7.42 (m, 6H), 6.00 (d, J=10 Hz, 1H), 5.80 (dd, J=10 and 6 Hz, 1H), 5.54 (m, 1H), 5.34 (m, 1H), 4.71 (m, 1H), 4.28 (m, 1H), 2.63-2.23 (m), 2.08-1.20 (m), 1.15 (s, 3H), 1.14 (s, 3H), 1.14 (d, J=7 Hz, 3H), 1.09 (s, 9H), 0.91 (d, J=7 Hz, 3H), 0.84 (t, J=7 Hz, 3H)

Step 2: Preparation of 6(R)-[2-[8(S)-(2,2-dimethylbutyryloxy)-2(S)-methyl-4a(R),5(S)-epoxy-6(R)-methyl-1,2,6,7,8,8a(R)-hexahydronaphthyl-1(S)]ethyl]-4(R)-tert-butyldiphenylsilyloxy-3,4,5,6-tetrahydro-2H-pyran-2-one (24).

To a stirred mixture of (23) (47.0 g, 72 mmol), NaHCO$_3$ (12.0 g, 0.14 mol), and EtOAc (600 mL) at 0° C. was added 55% meta-chloroperbenzoic acid (27.0 g, 86 mmol). After 1.0 h at 0° C. the reaction mixture was diluted with EtOAc, washed sequentially with 10% Na$_2$SO$_3$, H$_2$O, and brine, dried (MgSO$_4$), and concentrated. Flash chromatography (silica, 10% ethyl acetate/hexanes w/2% triethylamine) gave (24) as an oil.

TLC R$_f$=0.51 (silica, 30% ethyl acetate/hexanes); $^1$H NMR (CDCl$_3$) δ7.60 (m, 4H, 7.40 (m, 6H), 6.21 (dd, J=10 and 6 Hz, 1H), 5.12 (d, J=10 Hz, 1H), 5.11 (m, 1H), 4.68 (m, 1H), 4.24 (m, 1H), 2.96 (s, 1H), 2.60-2.28 (m, 5H), 2.01 (dd, J=12 and 4 Hz, 1H), 1.90-1.20 (m), 1.16 (d, J=7Hz, 3H), 1.12 (s, 3H), 1.10 (s, 3H), 1.04 (s, 9H), 0.96 (d, J=7 Hz, 3H), 0.80 (t, J=7 Hz, 3H).

Step 3: Preparation of 6(R)-[2-[8(S)-(2,2-dimethylbutyryloxy)-2(S)-methyl-5-oxo-6(R)-methyl-1,2,4a(R),6,7,8,8a(R)-heptahydronaphthyl-1(S)]ethyl]-4(R)-tert-butyldiphenylsilyloxy-3,4,5-tetrahydro-2H-pyran-2-one (25).

A stirred solution of (24) (20.0 g, 30.0 mmol), toluene (150 mL), and ether (150 mL) at −15° C. was treated dropwise with boron trifluoride etherate (3.0 mL, 24.4 mmol) over a 5 minute period. After stirring for 20 minutes the reaction mixture was diluted with ether, washed with sat. NaHCO$_3$, H$_2$O, and brine, dried (MgSO$_4$), and concentrated. Flash chromatography (silica, 12% ethylacetate/hexanes) furnished crude (25) as an oil.

TLC R$_f$=0.42 (silica, 30% ethyl acetate/hexanes); $^1$H NMR (CDCl$_3$) δ7.62 (m, 4H) 7.40 (m, 6H), 5.98 (d, J=10 Hz, 1H), 5.84 (m, 1H), 5.31 (m, 1H), 4.72 (m, 1H), 4.18 (m, 1H), 3.48 (bd, J=10 Hz, 1H), 2.63-2.23 (m, 3H), 1.95-1.10 (m), 1.25 (d, J=7 Hz, 3H), 1.19 (s, 3H), 1.18 (s, 3H), 1.10 (s, 9H), 0.88 (t, J=7 Hz, 3H), 0.85 (d, J=7 Hz, 3H).

Step 4: Preparation of 6(R)-[2-[8(S)-(2,2-dimethylbutyryloxy)-2(S)-methyl-5(R)-hydroxy-6(R)-methyl-1,2,4a(R),5,6,7,8,8a(R)-octahydronaphthyl-1(S)]ethyl]-4(R)-tert-butyldiphenylsilyloxy-3,4,5,6-tetrahydro-2H-pyran-2-one (26).

To a stirred solution of (25) (6.4 g, 9.5 mmol), THF (90 mL), and H$_2$O (5 mL) at 0° C. was added 0.36 g (0.95 mmol) NaBH$_4$ in one portion. After 20 minutes at 0° C. the reaction mixture was diluted with ether, washed with H$_2$O (2×) and brine, dried (MgSO$_4$), and concentrated. Flash chromatography (silica, 20% ethyl acetate/hexanes) gave (26) as a colorless oil.

TLC R$_f$=0.30 (silica, 35% ethyl acetate/hexanes); $^1$H NMR (CDCl$_3$) δ7.62 (m, 4H), 7.45 (m, 6H), 5.96 (d, J=10 Hz, 1H), 5.80 (m, 1H), 5.08 (m, 1H), 4.72 (m, 1H), 4.28 (m, 1H), 3.47 (m, 1H), 2.62-2.10 (m, 5H), 1.85-1.20 (m), 1.16 (s, 3H), 1.15 (s, 3H), 1.10 (d, J=7 Hz, 3H), 1.07 (s, 9H), 0.85 (t, J=7 Hz, 3H), 0.85 (t, J=7 Hz, 3H).

Step 5: Preparation of 6(R)-[2-[8(S)-(2,2-dimethylbutyryloxy)-2(S)-methyl-5(R)-hydroxy-6(R)-methyl-1,2,4a(R),5,6,7,8a(R)-octahydronaphthyl-1(S)]ethyl]-4(R)-hydroxy-3,4,5,6-tetrahydro-2H-pyran-2-one (I-27).

A premixed solution of tetrabutylammonium fluoride (1 M in THF, 1 mL, 16.0 mmol) and HOAc (0.92 mL, 16.0 mmol) was added in one portion to a stirred solution of (26) (3.6 g, 5.3 mmol) in THF (32 mL) followed by heating at 50° C. for 3.0 hours. The cooled reaction mixture was diluted with ether, washed with H$_2$O (2×) and brine, dried (MSO$_4$), and concentrated. Flash chromatography (silica, 70% ethyle acetate/hexanes) gave (I-27) as a solid. Recrystallization (ethyl acetate/hexanes) gave (I-27) as colorless needless mp=130°-132° C.

TLC R$_f$=0.39 (silica, ethyl acetate); $^1$H NMR (CDCl$_3$) δ5.95 (d, J=12 Hz, 1H), 5.79 (m, 1H), 5.11 (m, 1H), 4.60 (m, 1H), 4.38 (m, 1H), 3.49 (dt, J=11 and 6 Hz, 1H), 2.74 (dd, J=17 and 5 Hz, 1H), 2.61 (m, 1H), 2.48 (m, 1H), 2.30 (m, 1H), 2.18 (m, 1H), 2.05-1.20 (m), 1.17 (s, 3H), 1.16 (s, 3H), 1.09 (d, J=7 Hz, 3H), 0.86 (t, J=7 Hz, 3H), 0.85 (d, J=7 Hz, 3H)

EXAMPLES 8-39

Utilizing the general procedures of Examples 1-7, the following compounds of formula (I) are prepared from the appropriately substituted starting materials.

| Compound No. | R$_4$ | R$_5$ | R$_6$ | a |
|---|---|---|---|---|
| 28 | CH$_3$ | H | O$_2$COCH$_3$ | — |
| 29 | CH$_3$ | O$_2$COCH$_3$ | H | — |
| 30 | CH$_3$ | H | O$_2$CCH$_3$ | — |
| 31 | CH$_3$ | O$_2$CCH$_3$ | H | — |
| 32 | H | OH | H | — |
| 33 | H | H | OH | — |
| 34 | CH$_2$OH | OH | H | — |
| 35 | CH$_2$OH | H | OH | — |
| 36 | CH$_2$Ph | OH | H | — |
| 37 | CH$_2$Ph | H | OH | — |
| 38 | CH$_2$O$_2$CPh | H | OH | — |
| 39 | CH$_2$O$_2$CPh | OH | H | — |
| 40 | CH$_2$OH | O | O | — |
| 41 | CH$_2$Ph | O | O | — |
| 42 | H | O | O | — |
| 43 | CH$_2$OH | OCH$_2$Ph | H | — |
| 44 | CH$_2$OH | H | OCH$_2$PH | — |
| 45 | CH$_3$ | OCH$_2$CH$_3$ | H | — |
| 46 | CH$_3$ | H | OCH$_2$CH$_3$ | — |
| 47 | (CH$_2$)$_2$ | OH | H | — |
| 48 | (CH$_2$)$_2$ | H | OH | — |
| 49 | CH$_3$ | (CH$_2$)$_2$ | | — |
| 50 | CH$_2$OH | OH | H | db |
| 51 | CH$_2$OH | H | OH | db |
| 52 | H | OH | H | db |
| 53 | H | H | OH | db |
| 54 | CH$_2$Ph | OH | H | db |
| 55 | CH$_2$Ph | H | OH | db |
| 56 | CH$_3$ | OCH$_2$CH$_3$ | H | db |
| 57 | CH$_3$ | H | OCH$_2$CH$_3$ | db |
| 58 | CH$_3$ | H | O$_2$COCH$_3$ | db |

— = single bond
db = double bond
R$_5$ = R$_6$ = O means C=O

EXAMPLE 40

Preparation of Ammonium Salts of Compounds II

The lactone (1.0 mmol) from Example 1 Step 4 is dissolved with stirring in 0.1N NaOH (1.1 mmol) at ambient temperature. The resulting solution is cooled and acidified by the dropwise addition of 1N HCl. The

EXAMPLE 41

Preparation of Alkali and Alkaline Earth Salts of Compounds II

To a solution of 44 mg of lactone from Example 1 Step 4 in 2 ml of ethanol is added 1 ml of aqueous 0.1N NaOH. After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 42

Preparation of Ethylenediamine Salts of Compounds II

To solution of 0.50 g of the ammonium salt from Example 40 in 10 ml of methanol is added 0.04 ml of ethylenediamine. The methanol is stripped off under vacuum to obtain the desired ethylenediamine salt.

EXAMPLE 43

Preparation of Tris(hydroxymethyl)aminomethane Salts of Compounds II

To a solution of 202 mg of the ammonium salt from Example 40 in 5 ml of methanol is added a solution of 50 mg of tris(hydroxymethyl)aminomethane is 5 ml of methanol. The solvent is removed in vacuo to afford the desired tris(hydroxymethyl)aminomethane salt.

EXAMPLE 44

Preparation of L-Lysine Salts of Compounds II

A solution of 0.001 mole of L-lysine and 0.0011 mole of the ammonium salt from Example 40 in 15 ml of 85% ethanol is concentrated to dryness in vacuo to give the desired L-lysine salt.

Similarly prepared are the L-arginine, L-ornithine, and N-methyglucamine salts.

EXAMPLE 45

Preparation of Tetramethylammonium Salts of Compounds II

A mixture of 68 mg of ammonium salt from Example 40 in 2 ml of methylene chloride and 0.08 ml of 24% tetramethylammonium hydroxide in methanol is diluted with ether to yield the desired tetramethylammonium salt.

EXAMPLE 46

Preparation of Methyl Esters of Compounds II

To a solution of 400 mg of lactone from Example 1 Step 4 in 100 ml of absolute methanol is added 10 ml 0.1M sodium methoxide in absolute methanol. This solution is allowed to stand at room temperature for one hour, then is diluted with water and extracted twice with ethyl acetate. The organic phase is separated, dried ($Na_2SO_4$), filtered and evaporated in vacuo to yield the desired methyl ester.

In like manner, by the use of equivalent amounts of the alkoxides derived from propanol, butanol, isobutanol, t-butanol, amyl alcohol, isoamyl alcohol, 2-dimethylaminoethanol, benzyl alcohol, phenethanolm 2-acetamidoethanol and the like, and employing the corresponding alcohol, phenethanol, 2-acetamidoethanol and the like, and employing the corresponding alcohol as solvent, the corresponding esters are obtained.

EXAMPLE 47

Preparation of Free Dihydroxy Acids

The sodium salt of the compound II from Example 41 is dissolved in 2 ml of ethanol-water (1:1; v:v) and added to 10 ml of 1N hydrochloric acid from which the dihydroxy acid is extracted with ethyl acetate. The organic extract is washed once with water, dried ($Na_2SO_4$), and evaporated in vacuo with a bath temperature not exceeding 30° C. The dihydroxy acid derivative derived slowly reverts to the corresponding parent lactone on standing at room temperature. The dihydroxy acid form can be maintained by increasing the pH about 7.0.

EXAMPLE 48

As a specific embodiment of a composition of this invention, 20 mg of lactone from Example 1 Step 4 is formulated with sufficient finely divided lactose to provide a total amount of 580 to 590 mg to fill a size 0, hard-gelatin capsule.

What is claimed is:

1. A compound represented by the structural formula[e (I) or ] (II):

wherein:

$R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkylS(O)$_n$ in which n is 0 to 2,
  (j) $C_{3-8}$ cycloalkylS(O)$_n$,
  (k) phenylS(O)$_n$,
  (l) substituted phenylS(O)$_n$ in which the substituents are X and Y and
  (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
  (a) $C_{1-10}$ alkyl (b) substituted $C_{1-10}$ alkyl in which the substituent is selected from
  (i) halogen,
  (ii) hydroxy,
  (iii) $C_{1-10}$ alkoxy,
  (iv) $C_{1-5}$ alkoxycarbonyl,
  (v) $C_{1-5}$ acyloxy,
  (vi) phenyl,
  (vii) substituted phenyl in which the substituents are X and Y,
  (viii) $C_{1-10}$ alkylS(O)$_n$,
  (ix) $C_{3-8}$ cycloalkylS(O)$_n$,
  (x) phenylS(O)$_n$,
  (xi) substituted phenylS(O)$_n$ in which the substituents are X and Y, and
  (xii) oxo,
(c) $C_{1-10}$ alkylS(O)$_n$,
(d) $C_{3-8}$ cycloalkylS(O)$_n$,
(e) phenylS(O)$_n$,
(f) substituted phenylS(O)$_n$ in which the substituents are X and Y,
(g) halogen,
(h) hydroxy,
(i) $C_{1-10}$ alkoxy,
(j) $C_{1-5}$ alkoxycarbonyl,
(k) $C_{1-5}$ acyloxy,
(l) phenyl, and
(m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) $R_{10}$S in which $R_{10}$ is selected from
  (a) $C_{1-10}$ alkyl,
  (b) phenyl, and
  (c) substituted phenyl in which the substituents are X and Y;
$R_4$ is:
(1) hydrogen;
(2) $C_{1-10}$ alkyl; and
(3) substituted $C_{1-10}$ alkyl in which one or more substituents is selected from
  (a) halogen
  (b) hydroxy,
  (c) $C_{1-10}$ alkoxy
  (d) $C_{1-5}$ alkoxycarbonyl,
  (e) $C_{1-5}$ alkylacyloxy,
  (f) phenylacyloxy,
  (g) phenoxycarbonyl,
  (h) phenyl $C_{1-5}$ alkylacyloxy,
  (i) phenyl $C_{1-5}$ alkoxy,
  (j) amino,
  (k) $C_{1-5}$ alkylamino,
  (l) di($C_{1-5}$ alkyl)amino,
  (m) phenylamino,
  (n) substituted phenylamino in which the substituents are X and Y,
  (o) phenyl $C_{1-5}$ alkylamino,
  (p) substituted phenyl $C_{1-5}$ alkylamino in which the substituents are X and Y,
  (q) $C_{3-8}$ cycloalkyl,
  (r) phenyl,
  (s) substituted phenyl in which the substituents are X and Y,
  (t) phenylS(O)$_n$,
  (u) substituted phenyl S(O)$_n$ in which the substituents are X and Y,
  (v) phenyl $C_{1-5}$ alkyl S(O)$_n$,
  (w) $C_{1-5}$ alkylS(O)$_n$;
  (x) phenylaminoacyloxy,
  (y) $C_{1-5}$alkylaminoacyloxy,
  (z) $C_{1-5}$alkylacylamino,
  (aa) di(phenyl$C_{1-5}$alkyl)phosphonyl
  (bb) di($C_{1-5}$alkyl)phosphinyl
(4) $R_4$ together with the carbon atom to which it is attached represents a $C_{3-8}$ carbocyclic ring;
$R_5$ and $R_6$ independently are H, OH, OR$_7$ or $R_5$ and $R_6$ together with the carbon to which they are attached represent C=O or $R_5$ and $R_6$ together with the carbon to which they are attached represent a carbocyclic ring of 3 to 7 atoms; provided that when $R_5$ is H, $R_6$ is OH or OR$_7$, and when $R_5$ is OH, $R_6$ is H, and when $R_5$ is OR$_7$, $R_6$ is H;
$R_7$ is

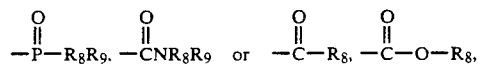

phenyl$C_{1-3}$alkyl, $C_{1-5}$alkyl;
$R_8$ and $R_9$ independently are H, $C_{1-3}$alkyl, phenyl$C_{1-3}$alkyl or aryl wherein aryl is phenyl, naphthyl,, or phenyl, or naphthyl substituted with groups X and Y; provided that when $R_7$ is

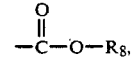

$R_8$ is not H and when $R_7$ is

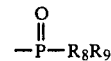

neither $R_8$ nor $R_9$ is H;
X and Y are independently selected from:
  a) OH;
  b) halogen,
  c) trifluoromethyl,
  d) $C_{1-3}$alkoxy,
  e) $C_{1-3}$alkylocarbonyloxy,
  f) phenylcarbonyloxy,
  g) $C_{1-3}$alkoxycarbonyl,
  h) phenyloxycarbonyl,
  i) hydrogen,
  j) $C_{1-5}$alkyl;
Z is selected from:
(1) hydrogen;
(2) $C_{1-5}$alkyl;
(3) substituted $C_{1-5}$ in which the substituent is selected from:
  (a) phenyl,
  (b) dimethylamino, and
  (c) acetylamino, and
(4) 2,3-dihydroxypropyl; halogen is Cl or F;

a is a single bond or a double bond; provided that when a is a double bond and $R_5$ or $R_6$ is OH or phenyl $C_{1-3}$alkoxy, the configuration of the 5-position is α-5-hydroxy or α-5-phenyl$C_{1-3}$alkoxy as represented in formula (II')

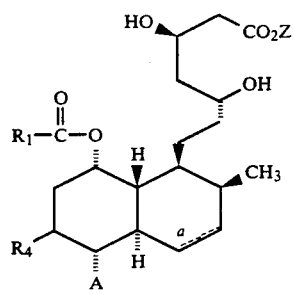

(II')

wherein A is OH or phenyl$C_{1-3}$alkoxy; or a pharmaceutically acceptable salt thereof.

2. A Compound of claim 1 wherein:
$R_4$ is;
(1) hydrogen;
(2) $C_{1-10}$ alkyl;
(3) substituted $C_{1-10}$ alkyl in which one or more substituents is selected from:
 (a) halogen,
 (b) hydroxy,
 (c) amino,
(4) $CH_2R_{12}$ in which $R_{12}$ is selected from:
 (a) $C_{1-5}$ alkoxy,
 (b) $C_{1-5}$ alkoxy carbonyl,
 (c) $C_{1-5}$ alkylacyloxy,
 (d) phenylacyloxy,
 (e) phenoxycarbonyl,
 (f) phenyl$C_{1-5}$alkyl,
 (g) phenyl$C_{1-5}$alkoxy,
 (h) $C_{1-5}$alkylamino,
 (i) di($C_{1-5}$alkyl)amino,
 (j) phenylamino,
 (k) substituted phenylamino in which the substituents are X and Y,
 (l) phenyl $C_{1-5}$alkylamino,
 (m) substituted phenyl$C_{1-5}$alkyl amino in which the substituents are X and Y,
 (n) $C_{3-8}$ cycloalkyl,
 (o) phenyl,
 (p) substituted phenyl in which the substituents are X and Y,
 (q) phenylS(O)$_n$
 (r) substituted phenylS(O)$_n$ in which the substituents are X and Y,
 (s) phenyl $C_{1-5}$ alkylS(O)$_n$,
 (t) $C_{1-5}$ alkylS(O)$_n$,
 (u) phenylaminoacyloxy,
 (v) $C_{1-5}$ alkylaminoacyloxy,
 (w) $C_{1-5}$ alkylacylamino,
 (x) di(phenyl$C_{1-5}$alkyl)phosphonyl,
 (y) di($C_{1-5}$alkyl)phosphinyl;
(5) $R_4$ together with the carbon atom to which it is attached represents a cyclopropane ring;

$R_5$ and $R_6$ independently are H, OH, OR$_7$, or $R_5$ and $R_6$ together with the carbon to which they are attached represent C=O, or $R_5$ and $R_6$ together with the carbon to which they are attached represent a cyclopropane ring; provided that when $R_5$ is H, $R_6$ is OH or OR$_7$ and when $R_5$ is OH, $R_6$ is H, and when $R_5$ is OR$_7$, $R_6$ is H;

X and Y are independently selected from:
 a) OH,
 b) F,
 c) trifluoromethyl,
 d) $C_{1-3}$alkoxy,
 e) hydrogen,
 f) $C_{1-5}$alkyl.

3. A Compound of claim 4 wherein:
$R_1$ is $C_{1-10}$alkyl; and
$R_4$ is $CH_3$, H, or $CH_2$phenyl.

4. A Compound of claim 3 wherein:
$R_7$ is

$C_{1-5}$alkyl or phenyl$C_{1-3}$alkyl;
$R_8$ and $R_9$ independently are H, $C_{1-3}$alkyl, phenyl$C_{1-3}$alkyl or aryl wherein aryl is phenyl or naphthyl or phenyl or naphthyl substituted with X.

5. A Compound of claim 4 wherein:
$R_1$ is 2-butyl or 2-methyl-2-butyl;
$R_4$ is $CH_3$.

6. A Compound of claim 2 wherein:
$R_1$ is $C_{1-10}$alkyl;
$R_4$ is $CH_2OH$ or phenylacyloxymethyl.

7. A Compound of claim 6 wherein:
$R_7$ is

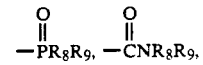

$C_{1-5}$alkyl or phenyl$C_{1-5}$alkyl;
$R_8$ and $R_9$ independently are H, $C_{1-3}$alkyl, phenyl$C_{1-3}$alkyl or aryl wherein aryl is phenyl or naphthyl or phenyl or naphthyl substituted with X.

8. A Compound of claim 7 wherein:
$R_1$ is 2-butyl or 2-methyl-2-butyl;
$R_4$ is $CH_2OH$.

9. A hypocholesterolemic, hypolipidemic pharmaceutical composition comprising a pharmaceutically acceptable carrier and a therapeutically effective amount of a compound as defined in claim 1.

10. A method of inhibiting cholesterol biosynthesis comprising the administration to a subject in need of such treatment a therapeutically effective amount of a compound of claim 1.

11. A method of treating hyperchloesterolemia to a subject in need of such treatment which comprises the administration of an antihyperchloesterolemic effective amount of a compound of claim 1.

12. A compound of claim 5 selected from the group consisting of:
7-[1,2,3,4,4a(R),5,6,7,8,8a(R)-decahydro-2(S)-methyl-5(R)-hydroxy-6(R)-methyl8(S)-(2,2-dimethyl-butyryloxy)-1(S)-naphthyl]-3(R),5(R)-dihydroxyheptanoic acid;
7-[1,2,3,4,4a(R),5,6,7,8,8a(R)-decahydro-2-(S)-methyl-5(S)-hydroxy-6(S)-methyl-8(S)-(2,2-dimethyl-butyryloxy)-1(S)-naphthyl]-3(R),5(R)-dihydroxyheptanoic acid.

13. A compound of claim 5 selected from the group consisting of:

7-[1,2,3,4,4a(R),5,6,7,8,8a(R)-decahydro-2(S)-methyl-5(R)-benzylaminocarbonyloxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-diphenylphosphinyloxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-(1-phenylethyl-2-oxy)-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-dibenzylaminocarbonyloxy-6(R)-methyl-8(S)-(2,2-dimethylbutyryloxy)-1(S)-naphthyl]-3(R),5(R)-dihydroxyheptanoic acid.

14. A compound of claim 5 which is:
7-[1,2,3,4,4a(R),5,6,7,8,7a(R)-decahydro-2(S)-methyl-5(R)-hydroxy-6(S)-methyl-8(S)-(2,2-dimethylbutyryloxy)-1(S)-naphthyl]-3(R),5(R)-dihydroxyheptanoic acid.

15. A compound of claim 5 which is:
7-[1,2,4a(R),5,6,7,8,8a(R)-octahydro-2(S)-methyl-5(R)-hydroxy-6(R)-methyl-8(S)-(2,2-dimethylbutyryloxy)-1(S)-naphthyl]-3(R),5(R)-dihydroxyheptanoic acid.

16. A compound of claim 5 selected from:
7-[1,2,3,4,4a(R),5,6,7,8,8a(R)-nonahydro-2(S)-methyl-5-oxo-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8(R)-nonahydro-2(S)-methyl-5-oxo-6(S)-methyl-8(S)-(2,2-dimethylbutyryloxy)-1(S)-naphthyl]-3(R),5(R)-dihydroxyheptanoic acid.

17. A composition of claim 9 in which the compound is selected from the group consisting of:

7-[1,2,3,4,4a(R),5,6,7,8,8a(R)-decahydro-2(S)-methyl-5(R)-hydroxy--6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(S)-hydroxy-6(S)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-benzylaminocarrbonyloxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-diphenylphosphinyloxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-(1-phenylethyl-2-oxy)-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-dibenzylaminocarbonyloxy-6(R)-methyl-8(S)-(2,2-dimethylbutyryloxy)-1(S)-naphthyl]-3(R),5(R)-dihydroxyheptanoic acid;

7-[1,2,3,4,4a(R),6,7,8,8(R)-nonahydro-2(S)-methyl-5-oxo-6(R)-methyl-8(S)-(2,2-dimethylbutyryloxy)-1(S)-naphthyl]-3(R),5(R)-dihydroxyheptanoic acid;

7-[1,2,3,4,4a(R),6,7,8,8a(R)-nonahydro-2(S)-methyl-5-oxo-6(S)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8(R)-decahydro-2(S)-methyl-5(R)-hydroxy-6(S)-methyl-8(S)-(2,2-dimethylbutyryloxy)-1(S)-naphthyl]-3(R),5(R)-dihydroxyheptanoic acid;

7-[1,2,4a(R),5,6,7,8,8a(R)-octahydro-2(S)-methyl-5(R)-hydroxy-6(R)-methyl-8(S)-(2,2-dimethylbutyryloxy)-1(S)-naphthyl]-3(R),5((R)-dihydroxyheptanoic acid.

18. A method of claim 10 in which the compound is selected from:

7-[1,2,3,4,4a(R),5,6,7,8,8(R)-decahydro-2(S)-methyl-5(R)-hydroxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-hydroxy-6(S)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-benzylaminocarbonyloxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-diphenylphosphinyloxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-(1-phenylethyl-2-oxy)-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-dibenzylaminocarbonyloxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5-oxo-6(R)-methyl-8(S)-(2,2-dimethylbutyryloxy)-1(S)-naphthyl]-3(R),5(R)-dihydroxyheptanoic acid;

7-[1,2,3,4,4a(R),6,7,8,8a(R)-nonahydro-2(S)-methyl-5-oxo-6(S)-methyl-8(S)-(2,2-dimethylbuutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-hydroxy-6(S)-methyl-8(S)-(2,2-dimethylbutyryloxy)-1(S)-naphthyl]-3(R),5(R)-dihydroxyheptanoic acid;

7-[1,2,4a(R),5,6,7,8,8a(R)-octahydro-2(S)-methyl-5(R)-hydroxy-6(R)-methyl-8(S)-(2,2-dimethylbutyryloxy)-1(S)-naphthyl]-3(R),5(R)-dihydroxyheptanoic acid.

19. A method of claim 11 in which the compound is selected from:

7-[1,2,3,4,4a(R),5,6,7,8,8a(R)-decahydro-2(S)-methyl-5(R)-hydroxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(S)-hydroxy-6(S)-methyl-8(S)-(2,2-dimethylbutyryloxy)-1(S)-naphthyl]-3(R),5(R)-dihyhroxyheptanoic acid;

7-[1,2,3,4,4a(R),5,6,7,8,8a(R)-decahydro-2(S)-methyl-5(R)-benzylaminocarbonyloxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-diphenylphosphinyloxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-(1-phenylethyl-2-oxy)-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5(R)-dibenzylaminocarbonyloxy-6(R)-methyl-8(S)-(2,2-dimethylbutyryloxy)-1(S)-naphthyl]-3(R),5(R)-dihydroxyheptanoic acid;

7-[1,2,3,4,4a(R),5,6,7,8,8a(R)-decahydro-2(S)-methyl-5-oxo-6(R)-methyl-8(S)-(2,2-dimethylbutyryloxy)-1(S)-naphthyl]-3(R),5(R)-dihydroxyheptanoic acid;

7-[1,2,3,4,4a(R),6,7,8,8a(R)-nonahydro-2(S)-methyl-5-oxo-6(S-methyl-8(S)-(2,2-dimethylbutyryloxy)-1(S)-naphthyl]-3(R),5(R)-dihydroxyheptanoic acid;

7-[1,2,4a(R),5,6,7,8,8a(R)-decahydro-2(S)-methyl-5(R)-hydroxy-6(S)-methyl-8(S)-(2,2-dimethylbutyryloxy)-1(S)-naphthyl]-3(R),5(R)-dihydroxyheptanoic acid;

7-[1,2,4a(R),5,6,7,8,8a(R)-octahydro-2(S)-methyl-5(R)-hydroxy-6(R)-methyl-8(S)-(2,2-dimethylbutyryloxy)-1(S)-naphthyl]-3(R),5(R)-dihydroxyheptanoic acid.

* * * * *